US009498515B2

(12) United States Patent
Caggiano et al.

(10) Patent No.: US 9,498,515 B2
(45) Date of Patent: Nov. 22, 2016

(54) COMPOSITIONS AND METHODS FOR TREATMENT DURING NON-ACUTE PERIODS FOLLOWING CNS NEUROLOGICAL INJURY

(75) Inventors: Anthony Caggiano, Larchmont, NY (US); Jennifer Iaci, Boonton, NJ (US)

(73) Assignee: Acorda Therapeutics, Inc., Ardsley, NY (US)

( * ) Notice: Subject to any disclaimer, the term of this patent is extended or adjusted under 35 U.S.C. 154(b) by 197 days.

(21) Appl. No.: 13/059,206

(22) PCT Filed: Aug. 17, 2009

(86) PCT No.: PCT/US2009/004692
§ 371 (c)(1),
(2), (4) Date: Apr. 29, 2011

(87) PCT Pub. No.: WO2010/019275
PCT Pub. Date: Feb. 18, 2010

(65) Prior Publication Data
US 2011/0269682 A1 Nov. 3, 2011

Related U.S. Application Data

(60) Provisional application No. 61/189,191, filed on Aug. 15, 2008.

(51) Int. Cl.
*A61K 38/00* (2006.01)
*A61K 38/16* (2006.01)
*A61K 38/18* (2006.01)

(52) U.S. Cl.
CPC ........... *A61K 38/1883* (2013.01); *A61K 38/00* (2013.01)

(58) Field of Classification Search
None
See application file for complete search history.

(56) References Cited

U.S. PATENT DOCUMENTS

| 5,530,109 | A | 6/1996 | Goodearl et al. |
|---|---|---|---|
| 5,594,114 | A | 1/1997 | Goodearl et al. |
| 5,716,930 | A | 2/1998 | Goodearl et al. |
| 5,876,973 | A | 3/1999 | Marchionni |
| 6,087,323 | A | 7/2000 | Gwynne et al. |
| 6,635,249 | B1 | 10/2003 | Marchionni et al. |
| 6,750,196 | B1 | 6/2004 | Reh et al. |
| 6,890,751 | B2 | 5/2005 | Marchionni |
| 7,037,888 | B1 | 5/2006 | Sklar et al. |
| 7,094,749 | B1 | 8/2006 | Goodearl et al. |
| 7,285,531 | B1 | 10/2007 | Goodearl et al. |
| 7,319,019 | B1 | 1/2008 | Goodearl et al. |
| 7,776,817 | B2 | 8/2010 | Ford |
| 7,973,007 | B2 | 7/2011 | Ford |
| 8,410,050 | B2 | 4/2013 | Kim et al. |
| 2006/0019888 | A1* | 1/2006 | Zhou ............................. 514/12 |
| 2007/0155665 | A1 | 7/2007 | Ford |

FOREIGN PATENT DOCUMENTS

| RU | 2005124277 A | 2/2006 |
|---|---|---|
| WO | WO-92/18627 A1 | 10/1992 |
| WO | WO-94/03644 A1 | 2/1994 |
| WO | WO-94/26298 A1 | 11/1994 |
| WO | WO-9709425 A1 | 3/1997 |
| WO | WO-99/18976 A1 | 4/1999 |
| WO | WO-2008/140814 A1 | 11/2008 |
| WO | WO-2010/019275 A2 | 2/2010 |
| WO | WO-2010/030317 A2 | 3/2010 |

OTHER PUBLICATIONS

Abe et al. "The Neuroprotective Effect of Prostaglandin E2 EP1 Receptor Inhibition has a Wide Therapeutic Window, is Sustained in Time and is not Sexually Dimorphic." *J. Cereb. Blood Flow. Metab.* 29.1(2009):66-72.
Belayev et al. "Human Albumin Therapy of Acute Ischemic Stroke: Marked Neuroprotective Efficacy at Moderate Doses and With a Broad Therapeutic Window." *Stroke.* 32.2(2001):553-560.
Bian et al. "Neuregulin-1 Attenuated Doxorubicin-Induced Decrease in Cardiac Troponins." *Am. J. Physiol. Heart Circ. Physiol.* 297.6(2009):H1974-H1983.
Bublil et al. "The EGF Receptor Family: Spearheading a Merger of Signaling and Therapeutics." *Curr. Opin. Cell Biol.* 19.2(2007):124-134.
Buonanno et al. "Neuregulin and ErbB Receptor Signaling Pathways in the Nervous System." *Curr. Opin. Neurobiol.* 11.3(2001):287-296.
Burden et al. "Neuregulins and Their Receptors: A Versatile Signaling Module in Organogenesis and Oncogenesis." *Neuron.* 18.6(1997):847-855.
Busfield et al. "Characterization of a Neuregulin-Related Gene, Don-1, That is Highly Expressed in Restricted Regions of the Cerebellum and Hippocampus." *Mol. Cell. Biol.* 17.7(1997):4007-4014.
Carraway et al. "Neuregulin-2, a New Ligand of ErbB3/ErbB4-Receptor Tyrosine Kinases." *Nature.* 387(1997):512-516.
Chang et al. "Ligands for ErbB-Family Receptors Encoded by a Neuregulin-Like Gene." *Nature.* 387(1997):509-512.
Chen et al. "Expression of Multiple Neuregulin Transcripts in Postnatal Rat Brains." *J. Comp. Neurol.* 349.3(1994):389-400.
Corfas et al. "Differential Expression of ARIA Isoforms in the Rat Brain." *Neuron.* 14.1(1995):103-115.
Dohare et al. "Dose Dependence and Therapeutic Window for the Neuroprotective Effects of Curcumin in Thromboembolic Model of Rat." *Behav. Brain Res.* 193.2(2008):289-297.
Falls et al. "ARIA, a Protein That Stimulates Acetylcholine Receptor Syntehsis, is a Member of The Neu Ligand Family." *Cell.* 72.5(1993):801-813.
Falls. "Neuregulins: Functions, Forms, and Signaling Strategies." *Exp. Cell Res.* 284.1(2003):14-30.
Fawcett. "Recovery From Spinal Cord Injury: Regeneration, Plasticity and Rehabilitation." *Brain.* 132.Pt6(2009):1417-1418.

(Continued)

*Primary Examiner* — Olga N Chernyshev
(74) *Attorney, Agent, or Firm* — Mintz Levin Cohn Ferris Glovsky and Popeo, P.C.; John A. Bauer, Esq.; Linyu L. Mitra

(57) ABSTRACT

This invention relates to treatment of neuroinjury in a post-acute window or in a chronic period following neuroinjury.

16 Claims, 21 Drawing Sheets

(56) References Cited

OTHER PUBLICATIONS

Fukazawa et al. "Neuregulin-1 Protects Ventricular Myocytes From Anthracycline-Induced Apoptosis via erbB4-Dependent Activation of PI3-Kinase/Akt." *J. Mol. Cell Cardiol.* 35.12(2003):1473-1479.
Gassmann et al. "Aberrant Neural and Cardiac Development in Mice Lacking the ErbB4 Neuregulin Receptor." *Nature.* 378.6555(1995):390-394.
GenBank Accession No. AB005060, Nov. 11, 1997.
Higashiyama et al. "A Novel Brain-Derived Member of the Epidermal Growth Factor Family That Interacts With ErbB3 and ErbB4." *J. Biochem.* 122.3(1997):675-80.
Hijazi et al. "NRG-3 in Human Breast Cancers: Activation of Multiple erbB Family Proteins." *Int. J. Oncol.* 13.5(1998):1061-1067.
Holmes et al. "Identification of Heregulin, A Specific Activator of p185erbB2." *Science.* 256(1992):1205-1210.
Hynes et al. "ErbB Receptors and Signaling Pathways in Cancer." *Curr. Opin. Cell Biol.* 21.2(2009):177-184.
Iaci et al. "Glial Growth Factor 2 Promotes Functional Recovery With Treatment Initiated Up to 7 Days After Permanent Focal Ischemic Stroke." *Neuropharmacol.* 59.7-8(2010):640-649.
Kastin et al. "Neuregulin-1-β1 Enters Brain and Spinal Cord by Receptor-Mediated Transport." *J. Neurochem.* 88.4(2004):965-970.
Komjáti et al. "Poly(ADP-ribose) Polymerase Inhibition Protect Neurons and the White Matter and Regulates the Translocation of Apoptosis-Inducing Factor in Stroke." *Int. J. Mol. Med.* 13.3(2004):373-382.
Lee et al. "Requirement for Neuregulin Receptor erbB2 in Neural and Cardiac Development." *Nature.* 378.6555(1995):394-398.
Lemke. "Neuregulins in Development." *Mol. Cell. Neurosci.* 7.4(1996):247-262.
Liu et al. "Neuregulin-1/erbB-Activation Improves Cardiac Function and Survival in Models of Ischemic, Dilated, and Viral Cardiomyopathy." *J. Am. Coll. Cardiol.* 48.7(2006):1438-1447.
Marchionni et al. "Glial Growth Factors are Alternatively Spliced erbB2 Ligands Expressed in the Nervous System." *Nature.* 362(1993):312-318.
Meyer et al. "Distinct Isoforms of Neuregulin are Expressed in Mesenchymal and Neuronal Cells During Mouse Development." *PNAS.* 91.3(1994):1064-1068.
Meyer et al. "Isoform-Specific Expression and Function of Neuregulin." *Development.* 124(1997):3575-3586.
Meyer et al. "Multiple Essential Functions of Neuregulin in Development." *Nature.* 378(1995):386-390.
Nagata et al. "Solution Structure of the Epidermal Growth Factor-Like Domain of Heregulin-α, a Ligand for p180erb*B*-4." *EMBO J.* 13.15(1994):3517-3523.
Orr-Urtreger et al. "Neural Expression and Chromosomal Mapping of Neu Differentiation Factor to 8p12-p21." *PNAS.* 90.5(1993):1867-1871.
Özcelik et al. "Conditional Mutation of the ErbB2 (HER2) Receptor in Cardiomyocytes Leads to Dilated Cardiomyopathy." *PNAS.* 99.13(2002):8880-8885.
Peles et al. "Isolation of the Neu/HER-2 Stimulatory Ligand: A 44 kd Glycoprotein That Induces Differentiation of Mammary Tumor Cells." *Cell.* 69.1(1992):205-216.
Peles et al. "Neu and its Ligands: From an Oncogene to Neural Factors." *BioEssays.* 15.12(1993):815-824.
Pinkas-Kramarski et al. "Brain Neurons and Glial Cells Express Neu Differentiation Factor/Heregulin: A Survival Factor for Astrocytes." *PNAS.* 91.20(1994):9387-9391.
Pinkas-Kramarski et al. "Differential Expression of NDF/Neuregulin Receptors ErbB-3 and ErbB-4 and Involvement in Inhibition of Neuronal Differentiation." *Oncogene.* 15(1997):2803-2815.
Pinkas-Kramarski et al. "ErB Tyrosine Kinases and the Two Neuregulin Families Constitute a Ligand-Receptor Network." *Mol. Cell. Biol.* 18.10(1998):6090-6101.
Sawyer et al. "Neuregulin-1β for the Treatment of Systolic Heart Failure." *J. Mol. Cell Cardiol.* 51.4(2011):501-505.
Schulz et al. "Extended Therapeutic Window for Caspase Inhibition and Synergy With MK-801 in the Treatment of Cerebral Histotoxic Hypoxia." *Cell Death Differ.* 5.10(1998):847-857.
Stewart et al. "More 'Malignant' Than Cancer? Five-Year Survival Following a First Admission for Heart Failure." *Eur. J. Heart Fail.* 3.3(2001):315-322.
Sun et al. "Effectiveness of PSD95 Inhibitors in Permanent and Transient Focal Ischemia in the Rat." *Stroke.* 39.9(2008):2544-2553.
Sutherland et al. "Neuroprotection for Ischaemic Stroke: Translation From the Bench to the Bedside." *Int. J. Stroke.* 7.5(2012):407-418.
Tamura et al. "Focal Cerebral Ischaemia in the Rat: 1. Description of Technique and Early Neuropathological Consequences Following Middle Cerebral Artery Occlusion." *J. Cereb. Blood Flow Metab.*1.1(1981):53-60.
Tamura et al. "Focal Cerebral Ischaemia in the Rat: 2. Regional Cerebral Blood Flow Determined by [14C] Iodoantipyrine Autoradiography Following Middle Cerebral Artery Occlusion." *J. Cereb. Blood Flow Metab.*1.1(1981):61-69.
Wen et al. "Neu Differentiation Factor: A Transmembrane Glycoprotein Containing an EGF Domain and an Immunoglobulin Homology Unit." *Cell.* 69.3(1992):559-572.
Xu et al. "Extended Therapeutic Window and Functional Recovery After Intraarterial Administration of Neuregulin-1 After Focal Ischemic Stroke." *J. Cerebral Blood Flow Metab.* 26(2005):527-535.
Zhang et al. "Neuregulin-3 (NRG3): A Novel Neural Tissue-Enriched Protein That Binds and Activates ErbB4." *PNAS.* 94.18(1997):9562-9567.
Hayase et al. "Heparin-Binding EGF-Like Growth Factor (HB-EGF) in Traumatic Brain Injury." *Brain Pathol.* 7.4(1997):1377. (Abstract #P5.H.09).
Jin et al. "Post-Ischemic Administration of Heparin-Binding Epidermal Growth Factor-Like Growth Factor (HB-EGF) Reduces Infarct Size and Modifies Neurogenesis After Focal Cerebral Ischemia in the Rat." *J. Cerebral Blood Flow Metab.* 24.4(2004):399-408.
Tanaka et al. "Heparin-Beinding Epidermal Growth Factor-Like Growth Factor mRNA Expression in Neonatal Rat Brain With Hypoxic/Ischemic Injury." *Brain Res.* 827(1999):130-138.
Wang et al. "Cloning and Neuronal Expression of a Type III Newt Neuregulin and Rescue of Denervated, Nerve-Dependent Newt Limb Blastemas by rhGGF2." *J. Neurobiol.* 43.2(2000):150-158.
Xue et al. "Liposome-Mediated Glial Growth Factor 2 Gene Therapy in Brain Injury." *Natl. Med. J. China.* 86.33(2006):2352-2356. (Chinese Original and English Abstract).
Liu et al. "Glial Growth Factor Accelerates Functional Recovery of Injured Peripheral Nerve." *Orthop. J. Chin.* 7.9(2000):879-882. (Chinese original and English abstract).
Du et al. Very delayed infarction after mild focal cerebral ischemia: a role for apoptosis? J Cereb Blood Flow Metab. Mar. 1996;16(2):195-201.
Australian Office Action issued Sep. 18, 2014, in Australian Application No. 2009282455 (3 pages).
Canadian Office Action issued Jun. 9, 2015, in Canadian Application No. 2,734,766 (5 pages).
Chinese Office Action issued Sep. 13, 2012, in Chinese Application No. 200980136712.3 (6 pages).
Chinese Office Action issued Feb. 19, 2014, in Chinese Application No. 200980136712.3 (9 pages).
Chinese Office Action issued Sep. 23, 2014, in Chinese Application No. 200980136712.3 (5 pages).
European Search Report issued Feb. 13, 2012, in European Application No. 09806990.9 (2 pages).
European Search Opinion issued Feb. 13, 2012, in European Application No. 09806990.9 (2 pages).
European Office Action issued Sep. 3, 2013, in European Application No. 09806990.9 (3 pages).
European Office Action issued Oct. 24, 2014, in European Application No. 09806990.9 (2 pages).
Written Opinion of the International Search Authority issued Mar. 25, 2010, in Application No. PCT/US2009/004692 (3 pages).
International Preliminary Report on Patentability issued Feb. 15, 2011, in Application No. PCT/US2009/004692 (4 pages).

* cited by examiner

Figure 6A

Nucleotide Sequence & Deduced Acid Sequence of GGF2HBS5

```
GGAATTCCTT TTTTTTTTT TTTTTTTCTT NNTTTTTTT TGCCCTTATA CCTCTTCGCC      60
TTTCTGTGGT TCCATCCACT TCTTCCCCCT CCTCCTCCCA TAAACAACTC TCCTACCCCT    120
GCACCCCCAA TAAATAAATA AAAGGAGAG GGCAAGGGGG GAGGAGGAGG AGTGGTGCTG     180
CGAGGGGAAG GAAAAGGGAG GCAGGGGGAG AAGAGCCGGG CAGAGTCCGA ACCGACAGCC    240
AGAAGCCCGC ACCGCACCTCG CACC AGA AGA TGG CGA CGC GCC CCG CGC CGC     291
                              Met Arg Trp Arg Ala Pro Arg Arg

TCC GGG CGT CCC GGC CCC CGG GCC CAG CGC CGC CCC GGC TCC GCC GCC CGC  339
Ser Gly Arg Pro Gly Pro Arg Ala Gln Arg Arg Pro Gly Ser Ala Ala Arg

TCG TCG CCG CCG CTG CCG CTG CCA CTA CTG CTG CTG CTG CTG GGG ACC      387
Ser Ser Pro Pro Leu Pro Leu Pro Leu Leu Leu Leu Leu Leu Gly Thr
                                                  Val Cys Leu Thr Val
                                                            GGF-II 09

GCG GCC CTG GCG CCG GGG GCG GCC AAC GAG GCG GCT CCC GCG              435
Ala Ala Leu Ala Pro Gly Ala Ala Gly Asn Glu Ala Ala Pro Ala
Ala Ala Leu Pro Pro

GGG GCC TCG GTG TGC TAC TCG TCC CCG CCC AGC GTG GGA TCG CAG          483
Gly Ala Ser Val Cys Tyr Ser Ser Pro Pro Ser Val Gly Ser Gln
                        Ala Ser Pro Val Ser Val Gly Ser Gln
                                                GGF-II 08

GAG CTA GCT CAG CGC|GCC GCG GTG ATC GAG GTG AAG GGA AAG GTG CAC CCG  531
Glu Leu Ala Gln Arg|Ala Ala Val Ile Glu Val Lys Gly Lys Val His Pro
Glu Leu Val Gln Arg|Trp Phe Val Val Ile Glu Val Lys Gly Lys
                    GGF-II 04
```

Figure 6B

Nucleotide Sequence & Deduced Acid Sequence of GGF2HBS5

```
CAG CGG CAG CAG GGG GCA CTC GAC AGG AAG GCG GCG GCG GCG       579
Gln Arg Gln Gln Gly Ala Leu Asp Arg Lys Ala Ala Ala Ala

GGC GAG GCA GGG GCC TGG GGC GGC GAT CGC GAG CCG GCC GGC       627
Gly Glu Ala Gly Ala Trp Gly Gly Asp Arg Glu Pro Ala Gly

CCA CGG GCG GCG CTG GGG CCG GCC GAG GAG CCG CTG GCC AAC       675
Pro Arg Ala Ala Leu Gly Pro Ala Glu Glu Pro Leu Ala Asn

GGG ACC GTG CCC TCT TGG CCC ACC GCC GTG CCC AGC GGC GAG       723
Gly Thr Val Pro Ser Trp Pro Thr Ala Pro Val Pro Ser Ala Gly Glu

CCC GGG GAG GCG GCG CCC TAT CTG GTG AAG GTG CAC CAG TGG GCG   771
Pro Gly Glu Ala Ala Pro Tyr Leu Val Lys Val His Gln Val Trp Ala
                                     Lys Val His Glu Val Trp Ala
                                        GGF-II 01 & GGF-II 11

GTG AAA GCC GGG GGC TTG AAG AAG GAC TCG CTG CTC ACC GTG CGC CTG   819
Val Lys Ala Gly Gly Leu Lys Lys Asp Ser Leu Leu Thr Val Arg Leu
Ala Lys                           Asp Leu Leu Leu Xaa Val Leu
                                        GGF-II 10

GGC ACC TGG GCC CAC CCC GCC TTC CCC TGC GGG CTC AAG GAG       867
Gly Thr Trp Gly His Pro Ala Phe Pro Ser Cys Gly Arg Leu Lys Glu
Gly Ala Trp Gly Pro Pro Ala Phe Pro Val Xaa Tyr
        GGF-II 03

GAC AGC AGG TAC ATC TTC TTC ATG GAG CCC GAC GCC AAC AGC ACC AGC   915
Asp Ser Arg Tyr Ile Phe Phe Met Glu Pro Asp Ala Asn Ser Thr Ser
        Tyr Ile Phe Phe Met Glu Pro Gly Ala Xaa Ser Ser Gly
                        GGF-II 02
```

Figure 6C

Nucleotide Sequence & Deduced Acid Sequence of GGF2HBS5

```
CGC GCG CCG GCC GCC TTC CGA GCC TCT TTC CCC CCT CTG GAG ACG GGC    963
Arg Ala Pro Ala Ala Phe Arg Ala Ser Phe Pro Pro Leu Glu Thr Gly

CGG AAC CTC AAG AAG GAG GTC AGC GTC CGG TGC CTG AAG CGG TGC GCC   1011
Arg Asn Leu Lys Lys Glu Val Ser Arg Cys Leu Lys Arg Cys Ala

TTG CCT CCC CAA TTG AAA GAG ATG AAG AGC CAG GAA TCG GCT GCA GGT   1059
Leu Pro Pro Gln Leu Lys Glu Met Lys Ser Gln Glu Ser Ala Ala Gly

TCC AAA GTC CTT CGG TGT GAA ACC AGT TCT GAA TAC TCC TCT CTC       1107
Ser Lys Val Leu Arg Cys Glu Thr Ser Ser Glu Tyr Ser Ser Leu
    Leu Val Leu Arg
      GGF-II 06

AGA TTC AAG TGG TTC AAG AAT GGG GAA TTG AAT CGA AAA AAC AAA       1155
Arg Phe Lys Trp Phe Lys Asn Gly Glu Leu Asn Arg Lys Asn Lys

CCA CAA AAT ATC AAG ATA CAA AAA AAG CCA GGG AAG TCA GAA CTT CGC   1203
Pro Gln Asn Ile Lys Ile Gln Lys Lys Pro Gly Lys Ser Glu Leu Arg

ATT AAC AAA GCA TCA CTG GCT TCT GGA GAG TAT ATG TGC AAA GTG       1251
Ile Asn Lys Ala Ser Leu Ala Ser Gly Glu Tyr Met Cys Lys Val
                                Asp Gly Tyr Met Xaa Lys
                                GGF-II 12

ATC AGC TTA GGA AAT GAC AGT TCT GCC TCT AAT ATC ACC ATC GTG       1299
Ile Ser Leu Gly Asn Asp Ser Ser Ala Ser Asn Ile Thr Ile Val

GAA TCA AAC GCT ACA TCT ACA TCC ACT GGG ACA AGC CAT CTT GTA       1347
Glu Ser Asn Ala Thr Ser Thr Ser Thr Thr Gly Thr Ser His Leu Val
```

Figure 6D

Nucleotide Sequence & Deduced Acid Sequence of GGF2HBS5

```
AAA TGT GCG GAG AAG GAG AAA ACT TTC TGT GTG AAT GGA GGG GAG TGC       1395
Lys Cys Ala Glu Lys Glu Lys Thr Phe Cys Val Asn Gly Gly Glu Cys

TTC ATG GTG AAA GAC CTT TCA AAC CCC TCG AGA TAC TTG TGC AAG TGC       1443
Phe Met Val Lys Asp Leu Ser Asn Pro Ser Arg Tyr Leu Cys Lys Cys

CCA AAT GAG TTT ACT GGT GAT CGC TGC CAA AAC TAC GTA ATG GCC AGC       1491
Pro Asn Glu Phe Thr Gly Asp Arg Cys Gln Asn Tyr Val Met Ala Ser

TTC TAC AGT ACG TCC ACT CCC TTT CTG TCT CTG CCT GAA                    1530
Phe Tyr Ser Thr Ser Thr Pro Phe Leu Ser Leu Pro Glu

TAGGAGCATG CTCAGTTGGT GCTGCTTTCT TGTTGCTGCA TCTCCCCTCA GATTCCACCT      1590
AGAGCTAGAT GTGTCTTACC AGATCTAATA TTGACTGCCT CTGCCTGTCG CATGAGAACA      1650
TTAACAAAAG CAATTGTATT ACTTCCTCTG TTCGCGACTA GTTGGCTCTG AGATACTAAT      1710
AGGTGTGTGA GGCTCCGGAT GTTTCTGGAA TTGATATTGA ATGATGTGAT ACAAATTGAT      1770
AGTCAATATC AAGCAGTGAA ATATGATAAT AAAGGCATTT CAAAGTCTCA CTTTTATTGA      1830
TAAAATAAAA ATCATTCTAC TGAACAGTCC ATCTTCTTTA TACAATGACC ACATCCTGAA      1890
AAGGGTGTTG CTAAGCTGTA ACCGATATGC ACTTGAAATG ATGGTAAGTT AATTTTGATT      1950
CAGAATGTGT TATTTGTCAC AAATAAACAT AATAAAAGGA AAAAAAAAAA AAA            2003
```

Figure 7

EGFL1

```
AGC CAT CTT GTC AAG TGT GCA GAG AAA ACT TTC TGT GTG AAT     48
Ser His Leu Val Lys Cys Ala Glu Lys Thr Phe Cys Val Asn

GGA GGC GAG TGC TTC ATG GTG AAA GAC CTT TCA AAT CCC TCA AGA TAC     96
Gly Gly Glu Cys Phe Met Val Lys Asp Leu Ser Asn Pro Ser Arg Tyr

TTG TGC AAG TGC CCA AAT GAG TTT ACT GGT GAT CGC TGC CAA AAC TAC    144
Leu Cys Lys Cys Pro Asn Glu Phe Thr Gly Asp Arg Cys Gln Asn Tyr

GTA ATG GCC AGC TTC TAC AGT ACG TCC ACT CCC TTT CTG TCT CTG CCT    192
Val Met Ala Ser Phe Tyr Ser Thr Ser Thr Pro Phe Leu Ser Leu Pro

GAA TAG    198
Glu
```

Figure 8

EGFL2

```
AGC CAT CTT GTC AAG TGT GCA GAG AAG GAG AAA ACT TTC TGT GTG AAT    48
Ser His Leu Val Lys Cys Ala Glu Lys Glu Lys Thr Phe Cys Val Asn

GGA GGC GAG TGC TTC ATG GTG AAA GAC CTT TCA AAT CCC TCA AGA TAC    96
Gly Gly Glu Cys Phe Met Val Lys Asp Leu Ser Asn Pro Ser Arg Tyr

TTG TGC AAG TGC CAA CCT GGA TTC ACT GGA GCG AGA TGT ACT GAG AAT   144
Leu Cys Lys Cys Gln Pro Gly Phe Thr Gly Ala Arg Cys Thr Glu Asn

GTG CCC ATG AAA GTC CAA ACC CAA GAA AAA GCG GAG CTC TAC TAA       192
Val Pro Met Lys Val Gln Thr Gln Glu Lys Ala Glu Leu Tyr
```

Figure 9

EGFL3

```
AGC CAT CTT GTC AAG TGT GCA GAG AAG GAG AAA ACT TTC TGT GTG AAT    48
Ser His Leu Val Lys Cys Ala Glu Lys Glu Lys Thr Phe Cys Val Asn

GGA GGC GAG TGC TTC ATG GTG AAA GAC CTT TCA AAT CCC TCA AGA TAC    96
Gly Gly Glu Cys Phe Met Val Lys Asp Leu Ser Asn Pro Ser Arg Tyr

TTG TGC AAG TGC CCA AAT GAG TTT ACT GGT GAT CGC TGC CAA AAC TAC   144
Leu Cys Lys Cys Pro Asn Glu Phe Thr Gly Asp Arg Cys Gln Asn Tyr

GTA ATG GCC AGC TTC TAC AAA GCG GAG GAG CTC TAC TAA               183
Val Met Ala Ser Phe Tyr Lys Ala Glu Glu Leu Tyr
```

Figure 10

EGFL4

| | | | | | | | | | | | | | | | | |
|---|---|---|---|---|---|---|---|---|---|---|---|---|---|---|---|---|
| AGC | CAT | CTT | GTC | AAG | TGT | GCA | GAG | AAG | GAG | AAA | ACT | TTC | TGT | GTG | AAT | 48 |
| Ser | His | Leu | Val | Lys | Cys | Ala | Glu | Lys | Glu | Lys | Thr | Phe | Cys | Val | Asn | |
| GGA | GGC | GAG | TGC | TTC | ATG | GTG | AAA | GAC | CTT | TCA | AAT | CCC | TCA | AGA | TAC | 96 |
| Gly | Gly | Glu | Cys | Phe | Met | Val | Lys | Asp | Leu | Ser | Asn | Pro | Ser | Arg | Tyr | |
| TTG | TGC | AAG | TGC | CCA | AAT | GAG | TTT | ACT | GGT | GAT | CGC | TGC | CAA | AAC | TAC | 144 |
| Leu | Cys | Lys | Cys | Pro | Asn | Glu | Phe | Thr | Gly | Asp | Arg | Cys | Gln | Asn | Tyr | |
| GTA | ATG | GCC | AGC | TTC | TAC | AAG | CAT | CTT | GGG | ATT | GAA | TTT | ATG | GAG | AAA | 192 |
| Val | Met | Ala | Ser | Phe | Tyr | Lys | His | Leu | Gly | Ile | Glu | Phe | Met | Glu | Lys | |
| GCG | GAG | GAG | CTC | TAC | TAA | | | | | | | | | | | 210 |
| Ala | Glu | Glu | Leu | Tyr | | | | | | | | | | | | |

Figure 11

EGFL5

```
AGC CAT CTT GTC AAG TGT GCA GAG AAG GAG AAA ACT TTC TGT GTG AAT    48
Ser His Leu Val Lys Cys Ala Glu Lys Glu Lys Thr Phe Cys Val Asn

GGA GGC GAG TGC TTC ATG GTG AAA GAC CTT TCA AAT CCC TCA AGA TAC    96
Gly Gly Glu Cys Phe Met Val Lys Asp Leu Ser Asn Pro Ser Arg Tyr

TTG TGC AAG TGC CAA CCT GGA TTC ACT GGA GCG AGA TGT ACT GAG AAT   144
Leu Cys Lys Cys Gln Pro Gly Phe Thr Gly Ala Arg Cys Thr Glu Asn

GTG CCC ATG AAA GTC CAA ACC CAA GAA AAG TGC CCA AAT GAG TTT ACT   192
Val Pro Met Lys Val Gln Thr Gln Glu Lys Cys Pro Asn Glu Phe Thr

GGT GAT CGC TGC CAA AAC TAC GTA ATG GCC AGC TTC TAC AGT ACG TCC   240
Gly Asp Arg Cys Gln Asn Tyr Val Met Ala Ser Phe Tyr Ser Thr Ser

ACT CCC TTT CTG CTG TCT CCT GAA TAG                               267
Thr Pro Phe Leu Leu Ser Leu Pro Glu Glu
```

Figure 12

EGFL6

```
AGC CAT CTT GTC AAG TGT GCA GAG AAG GAG AAA ACT TTC TGT GTG AAT    48
Ser His Leu Val Lys Cys Ala Glu Lys Glu Lys Thr Phe Cys Val Asn

GGA GGC GAG TGC TTC ATG GTG AAA GAC CTT TCA AAT CCC TCA AGA TAC    96
Gly Gly Glu Cys Phe Met Val Lys Asp Leu Ser Asn Pro Ser Arg Tyr

TTG TGC AAG TGC CAA CCT GGA TTC ACT GGA GCG AGA TGT ACT GAG AAT   144
Leu Cys Lys Cys Gln Pro Gly Phe Thr Gly Ala Arg Cys Thr Glu Asn

GTG CCC ATG AAA GTC CAA ACC CAA GAA AAG TGC CCA AAT GAG TTT ACT   192
Val Pro Met Lys Val Gln Thr Gln Glu Lys Cys Pro Asn Glu Phe Thr

GGT GAT CGC TGC CAA AAC TAC GTA ATG GCC AGC TTC TAC AAA GCG GAG   240
Gly Asp Arg Cys Gln Asn Tyr Val Met Ala Ser Phe Tyr Lys Ala Glu

GAG CTC TAC TAA                                                   252
Glu Leu Tyr
```

Figure 13

| | | | | | | | | | | | | | | | | |
|---|---|---|---|---|---|---|---|---|---|---|---|---|---|---|---|---|
| agc | cat | ctt | gtc | aag | tgt | gca | gag | aag | gag | aaa | act | ttc | tgt | gtg | aat | 48 |
| Ser | His | Leu | Val | Lys | Cys | Ala | Glu | Lys | Glu | Lys | Thr | Phe | Cys | Val | Asn | |

| | | | | | | | | | | | | | | | | |
|---|---|---|---|---|---|---|---|---|---|---|---|---|---|---|---|---|
| gga | ggc | gag | tgc | ttc | atg | gtg | aaa | gac | ctt | tca | aat | ccc | tca | aga | tac | 96 |
| Gly | Gly | Glu | Cys | Phe | Met | Val | Lys | Asp | Leu | Ser | Asn | Pro | Ser | Arg | Tyr | |

| | | | | | | | | | | | | | | | | |
|---|---|---|---|---|---|---|---|---|---|---|---|---|---|---|---|---|
| ttg | tgc | aag | tgc | cca | aat | gag | ttt | act | ggt | gat | cgc | tgc | caa | aac | tac | 144 |
| Leu | Cys | Lys | Cys | Pro | Asn | Glu | Phe | Thr | Gly | Asp | Arg | Cys | Gln | Asn | Tyr | |

| | | | | | | | | | | | |
|---|---|---|---|---|---|---|---|---|---|---|---|
| gta | atg | gcc | agc | ttc | tac | aaa | gcg | gag | gag | ctc | tac | can | 183 |
| Val | Met | Ala | Ser | Phe | Tyr | Lys | Ala | Glu | Glu | Leu | Tyr | Gln | |

Figure 14

```
Lys Cys Ala Glu Lys Glu Lys Thr Phe Cys Val Asn Gly Gly Glu Cys
 1               5                  10                  15
Phe Met Val Lys Asp Leu Ser Asn Pro Ser Arg Tyr Leu Cys Lys Cys
             20                  25                  30
Pro Asn Glu Phe Thr Gly Asp Arg Cys Gln Asn Tyr Val Met Ala Ser
         35                  40                  45
Phe Tyr
    50
```

Figure 15

```
Lys Cys Ala Glu Lys Glu Lys Thr Phe Cys Val Asn Gly Gly Glu Cys
 1               5                  10                  15
Phe Met Val Lys Asp Leu Ser Asn Pro Ser Arg Tyr Leu Cys Lys Cys
             20                  25                  30
Gln Pro Gly Phe Thr Gly Ala Arg Cys Thr Glu Asn Val Pro Met Lys
         35                  40                  45
Val Gln
    50
```

Figure 16 - NRG2 alpha

```
Met Arg Arg Asp Pro Ala Pro Gly Phe Ser Met Leu Leu Phe Gly Val
Ser Leu Ala Cys Tyr Ser Pro Ser Leu Lys Ser Val Gln Asp Gln Ala
Tyr Lys Ala Pro Val Val Val Glu Gly Lys Val Gln Gly Leu Val Pro
Ala Gly Gly Ser Ser Ser Asn Ser Thr Arg Glu Pro Pro Ala Ser Gly
Arg Val Ala Leu Val Lys Val Leu Asp Lys Trp Pro Leu Arg Ser Gly
Gly Leu Gln Arg Glu Gln Val Ile Ser Val Gly Ser Cys Val Pro Leu
Glu Arg Asn Gln Arg Tyr Ile Phe Phe Leu Glu Pro Thr Glu Gln Pro
Leu Val Phe Lys Thr Ala Phe Ala Pro Leu Asp Thr Asn Gly Lys Asn
Leu Lys Lys Glu Val Gly Lys Ile Leu Cys Thr Asp Cys Ala Thr Arg
Pro Lys Leu Lys Lys Met Lys Ser Gln Thr Gly Gln Val Gly Glu Lys
Gln Ser Leu Lys Cys Glu Ala Ala Ala Gly Asn Pro Gln Pro Ser Tyr
Arg Trp Phe Lys Asp Gly Lys Glu Leu Asn Arg Ser Arg Asp Ile Arg
Ile Lys Tyr Gly Asn Gly Arg Lys Asn Ser Arg Leu Gln Phe Asn Lys
Val Lys Val Glu Asp Ala Gly Glu Tyr Val Cys Glu Ala Glu Asn Ile
Leu Gly Lys Asp Thr Val Arg Gly Arg Leu Tyr Val Asn Ser Val Ser
Thr Thr Leu Ser Ser Trp Ser Gly His Ala Arg Lys Cys Asn Glu Thr
Ala Lys Ser Tyr Cys Val Asn Gly Gly Val Cys Tyr Tyr Ile Glu Gly
Ile Asn Gln Leu Ser Cys Lys Cys Pro Asn Gly Phe Phe Gly Gln Arg
Cys Leu Glu Lys Leu Pro Leu Arg Leu Tyr Met Pro Asp Pro Lys Gln
Ser Val Leu Trp Asp Thr Pro Gly Thr Gly Val Ser Ser Ser Gln Trp
Ser Thr Ser Pro Ser Thr Leu Asp Leu Asn
```

Figure 17 - NRG2 beta

```
Met Arg Arg Asp Pro Ala Pro Gly Phe Ser Met Leu Leu Phe Gly Val
Ser Leu Ala Cys Tyr Ser Pro Ser Leu Lys Ser Val Gln Asp Gln Ala
Tyr Lys Ala Pro Val Val Val Glu Gly Lys Val Gln Gly Leu Val Pro
Ala Gly Gly Ser Ser Ser Asn Ser Thr Arg Glu Pro Pro Ala Ser Gly
Arg Val Ala Leu Val Lys Val Leu Asp Lys Trp Pro Leu Arg Ser Gly
Gly Leu Gln Arg Glu Gln Val Ile Ser Val Gly Ser Cys Val Pro Leu
Glu Arg Asn Gln Arg Tyr Ile Phe Phe Leu Glu Pro Thr Glu Gln Pro
Leu Val Phe Lys Thr Ala Phe Ala Pro Leu Asp Thr Asn Gly Lys Asn
Leu Lys Lys Glu Val Gly Lys Ile Leu Cys Thr Asp Cys Ala Thr Arg
Pro Lys Leu Lys Lys Met Lys Ser Gln Thr Gly Gln Val Gly Glu Lys
Gln Ser Leu Lys Cys Glu Ala Ala Ala Gly Asn Pro Gln Pro Ser Tyr
Arg Trp Phe Lys Asp Gly Lys Glu Leu Asn Arg Ser Arg Asp Ile Arg
Ile Lys Tyr Gly Asn Gly Arg Lys Asn Ser Arg Leu Gln Phe Asn Lys
Val Lys Val Glu Asp Ala Gly Glu Tyr Val Cys Glu Ala Glu Asn Ile
Leu Gly Lys Asp Thr Val Arg Gly Arg Leu Tyr Val Asn Ser Val Ser
Thr Thr Leu Ser Ser Trp Ser Gly His Ala Arg Lys Cys Asn Glu Thr
Ala Lys Ser Tyr Cys Val Asn Gly Gly Val Cys Tyr Tyr Ile Glu Gly
Ile Asn Gln Leu Ser Cys Lys Cys Pro Val Gly Tyr Thr Gly Asp Arg
Cys Gln Gln Phe Ala Met Val Asn Phe Ser
```

Fig 18

EGF-like domain can be defined as sub-domains of NRGs for which sequence alignment reveals at least 25, 26, 27, 28, 29, 30, 31, 32, 33, 34, 35, 36, 37, 38, 39, 40 % homology in amino acid sequence as compared to the human EGF molecule (sequence P01133|971-1023, at the bottom of the alignment below). Homologous amino acids have identical, conserved or semi-conserved physico-chemical and structural properties, as denoted by the symbols '*', ':' and '.', respectively.

```
Beta2region               TSHLVKCAEKEKTFCVNGGECFMVKDLSNPSRYLCKCPNEFTGDRCQNYVMASFYK------------------------AEELYQK---  63
Zensun                    -SHLVKCAEKEKTFCVNGGECFMVKDLSNPSRYLCKCPNEFTGDRCQNYVMASFYK------------------------AEELYQ----  61
156/416                   -SHLVKCAEKEKTFCVNGGECFMVKDLSNPSRYLCKCPNEFTGDRCQNYVMASFYK------------------------AEELY-----  60
RnD                       TSHLVKCAEKEKTFCVNGGECFMVKDLSNPSRYLCKCPNEFTGDRCQNYVMASFYK-------------IEFME-AEELYQK---        71
151                       ----KCAEKEKTFCVNGGECFMVKDLSNPSRYLCKCPNEFTGDRCQNYVMASFY---------------------------------    50
EGF-ld_NRGbeta3           ----KCAEKEKTFCVNGGECFMVKDLSNPSRYLCKCPNEFTGDRCQNYVMASFY---------------------------------    50
157/417seq                -SHLVKCAEKEKTFCVNGGECFMVKDLSNPSRYLCKCPNEFTGDRCQNYVMASFYKHLG----------IEFMEKAEELY-------   69
EGF-ld_GGF                ----KCAEKEKTFCVNGGECFMVKDLSNPSRYLCKCPNEFTGDRCQNYVMASFY---------------------------------    50
RnD_catno296HR            -SHLVKCAEKEKTFCVNGGECFMVKDLSNPSRYLCKCQPGFTGARCTENVPMKVQNQE---------------KAEELYQK-----   65
155/415_seqid200_seqid155 -SHLVKCAEKEKTFCVNGGECFMVKDLSNPSRYLCKCQPGFTGARCTENVPMKVQTQE---------------KAEELY-------   63
EGF-ld_NDF43              ----KCAEKEKTFCVNGGECFMVKDLSNPSRYLCKCQPGFTGARCTENVPMKVQ----------------------------    50
152                       ----KCAEKEKTFCVNGGECFMVKDLSNPSRYLCKCQPGFTGARCTENVPMKVQ----------------------------    50
159/419                   -SHLVKCAEKEKTFCVNGGECFMVKDLSNPSRYLCKCQPGFTGARCTENVPMKVQTQEKCPNEFTGDRCQNYVMASFYKAEELY---  83
158/418                   -SHLVKCAEKEKTFCVNGGECFMVKDLSNPSRYLCKCQPGFTGARCTENVPMKVQTQEKCPNEFTGDRCQNYVMASFYSTPFLSLPE  88
EGF-ld_NRGlgamma          ----KCAEKEKTFCVNGGECFMVKDLSNPSRYLCK--------------------------------------------------    37
EGF-ld_GGF2               ----KCAEKEKTFCVNGGECFMVKDLSNPSRYLCKCPNEFTGDRCQNYVMASFYSTS-------------TPFLSLPE--        61
EGF-ld_SMDF               ----KCAEKEKTFCVNGGECFMVKDLSNPSRYLCKCPNEFTGDRCQNYVMASFYSTS-------------TPFLSLPE--        61
154/414                   -SHLVKCAEKEKTFCVNGGECFMVKDLSNPSRYLCKCPNEFTGDRCQNYVMASFYSTS-------------TPFLSLPE--       65
P01133|971-1023           -NSDSECPLSHDGYCLHDGVCMYIEALD---KYACNCVVGYIGERCQ-YRDLKWWELR---------------------------   53
                          :*  ..  :*:...**.*:  :: .*.    :* *:
```

COMPOSITIONS AND METHODS FOR TREATMENT DURING NON-ACUTE PERIODS FOLLOWING CNS NEUROLOGICAL INJURY

CROSS-REFERENCE TO RELATED APPLICATIONS

The present application is a national phase application under 35 U.S.C. §371 of International Patent Application PCT Application No. PCT/US2009/004692, filed 17 Aug. 2009, which claims the benefit of U.S. Provisional Application No. 61/189,191, filed 15 Aug. 2008. The entire contents of these applications are incorporated herein by reference.

INCORPORATION-BY-REFERENCE OF SEQUENCE LISTING

The contents of the text file named "43509-515N01US_v3_ST25.txt", which was created on Apr. 30, 2015, and is 41 KB in size, are hereby incorporated by reference in their entirety.

FIELD OF THE INVENTION

The field of the invention relates to treatment of central nervous system neuroinjury. More specifically, the invention is directed to the administration of a neuregulin [e.g., glial growth factor 2 (GGF2)] to a subject during the non-acute or chronic period following traumatic neuroinjury.

BACKGROUND OF THE INVENTION

Central nervous system (CNS) injuries to are a serious health problem. This category of injury includes events such as ischemic injury, hemorrhagic injury, penetrating trauma and non-penetrating trauma. CNS injuries generally heal incompletely leaving the subject with some degree of permanent dysfunction ranging from extremely mild to death. The residual dysfunction may include motor, sensory, cognitive, emotional and autonomic abnormalities.

A key category of CNS neuroinjury comprises brain injury. Brain injury is a devastating condition that results in some degree of permanent disability including motor, sensory and cognitive deficits and emotional instability such as post traumatic stress disorder, attention deficit disorder, depression and emotional lability. Common causes of brain injury include ischemic stroke, hemorrhagic stroke, subdural hematoma, epidural hematoma, closed head injury (acceleration/deceleration, concussion and rotational), penetrating brain injury (gun shot wounds and other projectiles).

Stroke is the third-leading cause of death and the main cause of disability in the western world. Stroke, therefore, presents a large socioeconomic burden. The etiology of a stroke can be either ischemic, which is the case in the majority of strokes, or hemorrhagic. An ischemic stroke can be caused by a clot that forms elsewhere in the body and travels via the bloodstream to the brain (embolic stroke) or by a blood clot that forms inside the artery of the brain (thrombotic stroke). After massive cell death in the immediate infarct core due to lack of glucose and oxygen, the infarct area expands for days, owing to secondary mechanisms such as glutamate excitotoxicity, apoptotic mechanisms, and generation of free radicals. Following neuroinjuries (e.g. an ischemic event) animals and people may recover function over several days, weeks and months without any therapeutic. All too often, this recovery however is only partial and animals and people suffer from permanent disability which may include motor, sensory and cognitive deficits.

Risk factors that increase the likelihood of an individual having a stroke are well known. These include, and are not limited to, risk factors that can not be changed: advanced age, heredity, ace, gender, prior history of stroke or heart attack; and risk factors that can be changed, treated or controlled: high blood pressure, cigarette smoking, diabetes mellitus, carotid or other artery disease, atrial fibrillation, other heart disease, sickle cell disease, high blood cholesterol, poor diet, and physical inactivity and obesity.

To date, the non-palliative treatment of ischemic stroke is confined to therapeutics administered in the acute phase following a stroke. The acute phase ranges from the time of onset of the neuroinjury (e.g., stroke) to approximately six hours post-neuroinjury. The acute phase is followed by the semi-acute phase, which ranges from approximately six hours to two days post-neuroinjury. Accordingly, current non-palliative therapeutics are used in an attempt to reverse the occlusion of blood flow, restore oxygenation of the brain and limit the extent of lost brain structure. Other than tPA for acute use, there are no drugs are approved for the treatment of stroke. Patients remain with some level of dysfunction that at best may improve somewhat endogenously for approximately 60 days. This recovery may only be augmented by physical therapy. Unfortunately, many patients are left with permanent disability with little hope for improvement.

At present, the only drug approved by the Food and Drug Administration (FDA) for the treatment of ischemic stroke is tissue plasminogen activator (tPA). tPA is a serine protease that converts plasminogen to plasmin. Plasmin then breaks fibrin which is a component of the clots that occlude the vessels in the brain and cause strokes. It is ideally administered within three hours from the onset of symptoms. Generally, only 3% to 5% of individuals who suffer a stroke reach the hospital in time to be considered for this treatment. Ideally, tPA is administered within the first three hours post-occlusion, but may be administered by some clinicians as late as six hours post-occlusion. Unfortunately, the vast majority of patients who experience a stroke fail to reach the hospital in time to be considered for this treatment. For those patients who arrive at the hospital within the efficacious temporal window, tPA is administered in an attempt to reverse the occlusion of blood flow, restore oxygenation of the brain and limit the extent of lost brain structure. However, there are some significant contraindications that limit the ongoing use of tPA. After an initial period of about 3 to 6 hours, at most, tPA can cause intracerbral bleeding and hemorrhagic stroke. For such reasons, tPA is limited to administration during the acute phase in order to achieve any therapeutic efficacy.

To date no other therapy has been approved for the treatment of stroke. Other experimental therapies such as arterially delivered pro-urokinase are under investigation as potential means for disrupting clots and restoring blood flow. The scientific literature has, however, described many agents that have proven beneficial for protecting brain matter and restoring function in experimental animal models of stroke. All these agents focus on reducing acute cell death, inflammation, and apoptosis and must, therefore, be delivered within hours (some up to 24 hours) after the ischemic event. Heretofore, it is generally accepted that treatment for CNS injury such as stroke is required acutely (Abe et al., 2008, J Cereb Blood Flow Metab. July 23, Epub ahead of print, Sun et al., 2008, Stroke July 10, Epub ahead of print, pages not available yet); Dohare et al., 2008, Behav Brain Res. 193(2):289-97; Belayev et al., 2001, Stroke 32(2):553-60).

Such agents have not, however, been shown to limit damage to the brain, restore function or enhance recovery following stroke when administered after a lag time of several hours, at most in some experimental animal models about one day following stroke. The only therapy known to show efficacy days and weeks after a stroke is palliative or rehabilitative, such as occupational or physical therapy. Indeed, the present inventors are not aware of any agents or drugs that have been shown to enhance recovery days or weeks following stroke.

After an acute occlusion, there is often a localized area of destroyed brain matter that is surrounded by a penumbral zone that will die within hours if circulation is not restored. The time to death of this penumbral zone can be extended by a few hours in experimental models with neuroprotectants, such as NMDA antagonists, calcium channel blockers, radical scavengers and trapping agents, anti-apoptotics, caspase inhibitors, parp inhibitors, etc. For this purpose a "neuroprotectant" is something that can save neurons before they die from the variety of insults presented to them in the acute phase. After 24 to 48 hours, however, there is little hope for protecting cells from necrotic death and, while apoptotic death continues for several days (See FIG. 1 the therapeutic window for anti-apoptotic therapies has not proven to be much wider than acute protective therapies [Schulz et al., 1998, Cell Death Differ. 5(10):847-57; Komjati et al., 2004, Int J Mol. Med. 13(3):373-82].

Neuregulin exhibits neuroprotective properties which, like other agents described above, have shown benefit in reducing the disability seen if delivered to animals within hours after stroke. See U.S. application Ser. No. 09/530,884, the entire contents of which are incorporated herein by reference.

In view of the prevalence of neuroinjury, particularly with regard to stroke, there is a need for therapeutic agents that can be administered efficaciously to subjects to limit damage to the brain, restore function and/or enhance recovery following neuroinjury.

Neuregulins (NRGs) and NRG receptors comprise a growth factor-receptor tyrosine kinase system for cell-cell signaling that is involved in organogenesis in nerve, muscle, epithelia, and other tissues (Lemke, Mol. Cell. Neurosci. 7:247-262, 1996 and Burden et al., Neuron 18:847-855, 1997). The NRG family consists of four genes that encode numerous ligands containing epidermal growth factor (EGF)-like, immunoglobulin (Ig), and other recognizable domains. Numerous secreted and membrane-attached isoforms function as ligands in this signaling system. The receptors for NRG ligands are all members of the EGF receptor (EGFR) family, and include EGFR (or ErbB1), ErbB2, ErbB3, and ErbB4, also known as HER1 through HER4, respectively, in humans (Meyer et al., Development 124:3575-3586, 1997; Orr-Urtreger et al., Proc. Natl. Acad. Sci. USA 90: 1867-71, 1993; Marchionni et al., Nature 362:312-8, 1993; Chen et al., J. Comp. Neurol. 349:389-400, 1994; Corfas et al., Neuron 14:103-115, 1995; Meyer et al., Proc. Natl. Acad. Sci. USA 91:1064-1068, 1994; and Pinkas-Kramarski et al., Oncogene 15:2803-2815, 1997).

The four NRG genes, NRG-1, NRG-2, NRG-3, and NRG-4, map to distinct chromosomal loci (Pinkas-Kramarski et al., Proc. Natl. Acad. Sci. USA 91:9387-91, 1994; Carraway et al., Nature 387:512-516, 1997; Chang et al., Nature 387:509-511, 1997; and Zhang et al., Proc. Natl. Acad. Sci. USA 94:9562-9567, 1997), and collectively encode a diverse array of NRG proteins. The gene products of NRG-1, for example, comprise a group of approximately 15 distinct structurally-related isoforms (Lemke, Mol. Cell. Neurosci. 7:247-262, 1996 and Peles and Yarden, BioEssays 15:815-824, 1993). The first-identified isoforms of NRG-1 included Neu Differentiation Factor (NDF; Peles et al., Cell 69, 205-216, 1992 and Wen et al., Cell 69, 559-572, 1992), heregulin (HRG; Holmes et al., Science 256:1205-1210, 1992), Acetylcholine Receptor Inducing Activity (ARIA; Falls et al., Cell 72:801-815, 1993), and the glial growth factors GGF1, GGF2, and GGF3 (Marchionni et al. Nature 362:312-8, 1993).

The NRG-2 gene was identified by homology cloning (Chang et al., Nature 387:509-512, 1997; Carraway et al., Nature 387:512-516, 1997; and Higashiyama et al., J. Biochem. 122:675-680, 1997) and through genomic approaches (Busfield et al., Mol. Cell. Biol. 17:4007-4014, 1997). NRG-2 cDNAs are also known as Neural- and Thymus-Derived Activator of ErbB Kinases (NTAK; Genbank Accession No. AB005060), Divergent of Neuregulin (Don-1), and Cerebellum-Derived Growth Factor (CDGF; PCT application WO 97/09425). Experimental evidence shows that cells expressing ErbB4 or the ErbB2/ErbB4 combination are likely to show a particularly robust response to NRG-2 (Pinkas-Kramarski et al., Mol. Cell. Biol. 18:6090-6101, 1998). The NRG-3 gene product (Zhang et al., supra) is also known to bind and activate ErbB4 receptors (Hijazi et al., Int. J. Oncol. 13:1061-1067, 1998).

An EGF-like domain is present at the core of all forms of NRGs, and is required for binding and activating ErbB receptors. Deduced amino acid sequences of the EGF-like domains encoded in the three genes are approximately 30-40% identical (pairwise comparisons). Further, there appear to be at least two sub-forms of EGF-like domains in NRG-1 and NRG-2, which may confer different bioactivities and tissue-specific potencies Cellular responses to NRGs are mediated through the NRG receptor tyrosine kinases EGFR, ErbB2, ErbB3, and ErbB4 of the epidermal growth factor receptor family. High-affinity binding of all NRGs is mediated principally via either ErbB3 or ErbB4. Binding of NRG ligands leads to dimerization with other ErbB subunits and transactivation by phosphorylation on specific tyrosine residues. In certain experimental settings, nearly all combinations of ErbB receptors appear to be capable of forming dimers in response to the binding of NRG-1 isoforms. However, it appears that ErbB2 is a preferred dimerization partner that may play an important role in stabilizing the ligand-receptor complex. ErbB2 does not bind ligand on its own, but must be heterologously paired with one of the other receptor subtypes. ErbB3 does not possess tyrosine kinase activity, but is a target for phosphorylation by the other receptors. Expression of NRG-1, ErbB2, and ErbB4 is known to be necessary for trabeculation of the ventricular myocardium during mouse development.

SUMMARY OF THE INVENTION

The present invention presents a novel method for treating following neuroinjury in a mammal. The method is based on the observation that therapeutic benefits of a polypeptide that contains an epidermal growth factor-like (EGF-like) domain can be achieved by administering a therapeutically effective amount of the polypeptide to a mammal; in certain embodiments the treatment is performed at or after hour 1, hour 2, hour 8, hour 12, hour 24, hour 30, hour 36 hour 42, day 2 or later following neuroinjury. In one embodiment of the invention treatment is initiated after the acute window post-injury. In one embodiment of the invention treatment is initiated after the semi-acute window post-injury. In one embodiment of the invention treatment is initiated during and yet continues after the acute window post-injury. In one embodiment of the invention treatment is initiated during and yet continues after the semi-acute window post-injury.

Accordingly, the present invention comprises administration of a polypeptide (or nucleic acid encoding same) that contains an EGF-like domain to the mammal starting at day 1, 2 or 3 even up to and including days 4, 5, 6, 7, 8, 9, 10, 11, 12, 13, 14 days; a week or more than one week, two weeks or more than two weeks post-neuroinjury; three weeks or more than three weeks post-neuroinjury; four weeks or more than four weeks post-neuroinjury; one month or more than one month post-neural injury; two months or more than two months post-neural injury; three months or more than three months post-neural injury; four months or more than four months post-neural injury; five months or more than five months post-neural injury; six months or more than six months post-neural injury. In accordance with the present invention the EGF-like domain is encoded by a neuregulin gene. Administration in accordance with the invention comprises administration of a peptide comprising an EGF-like domain, or a nucleic acid molecule encoding same, in an amount effective to treat the chronic phase following neuroinjury in the mammal In accordance with another aspect of the invention, a method for promoting neurorecovery during a period outside the acute or semi-acute phase following an ischemic event in a mammal is presented. Treatment in accordance with the invention can begin within an acute or semi-acute period but includes at least one, two three, four, five, six or more than six treatments beyond the acute or semi-acute period, respectively.

A method of the invention comprises administering a polypeptide comprising an epidermal growth factor-like (EGF-like) domain to said mammal, wherein said EGF-like domain is encoded by the neuregulin (NRG)-1 gene, and said administering is performed at least two or three or four days after the ischemic event, although treatment can begin within the acute or semi acute time frame, and in a therapeutically effective amount sufficient to promote neurorecovery during the chronic phase following an ischemic event in said mammal.

In particular embodiments of the invention, the neuregulin gene may be the NRG-1 gene, the NRG-2 gene, the NRG-3 gene or the NRG-4 gene. A neuregulin polypeptide of the invention may, in turn, be encoded by any one of these four neuregulin genes; a neuregulin polypeptide of the invention may, in turn, be encoded by a variant or homologue of any one of these four neuregulin genes. See FIGS. 6A-6D for the amino and nucleic acid sequences of full length human GGF2 an isoform of NRG-1.

In an aspect of the invention, suitable mammals include, but are not limited to, mice, rats, rabbits, dogs, monkeys or pigs. In a more particular embodiment of the invention, the mammal is a human.

DEFINITIONS

As used herein, the term 'about' comprises the specified value plus or minus 1, 2, 3, 4, 5, 6, 7, 8, 9, 10, 11, 12, 13, 14, 15% of the specified value. In one embodiment "about" signifies 98-102% of the specified value. In one embodiment "about" signifies 95-105% of the specified value.

Post-injury, the "acute phase" ranges from the time of onset of the neuroinjury (e.g., stroke) to approximately six hours post-neuroinjury. The acute phase is followed by the "semi-acute phase", which ranges from approximately six hours to two days post-neuroinjury. In one embodiment the "semi-acute phase" ranges from approximately six hours to three days post-neuroinjury. The period following the semi-acute phase is referred to as the "chronic phase" post-neuroinjury. The post-acute phase includes both the semi-acute and chronic post-injury periods. n By "epidermal growth factor-like domain" or "EGF-like domain" is meant a polypeptide motif encoded by the NRG-1, NRG-2, or NRG-3 gene that binds to and activates ErbB2, ErbB3, ErbB4, or combinations thereof, and bears a structural similarity to the EGF receptor-binding domain as disclosed in Holmes et al., Science 256:1205-1210, 1992; U.S. Pat. No. 5,530,109; U.S. Pat. No. 5,716,930; U.S. Pat. No. 7,037,888; Hijazi et al., Int. J. Oncol. 13:1061-1067, 1998; Chang et al., Nature 387:509-512, 1997; Carraway et al., Nature 387:512-516, 1997; Higashiyama et al., J. Biochem. 122:675-680, 1997; and WO 97/09425). See FIGS. 7-12 for nucleic and amino acid sequences corresponding to EGFL domains 1-6 encoded by the NRG-1 gene.

By "expression vector" is meant a genetically engineered plasmid or virus, derived from, for example, a bacteriophage, adenovirus, retrovirus, poxvirus, herpesvirus, or artificial chromosome, that is used to transfer a polypeptide (e.g., a neuregulin) coding sequence, operably linked to a promoter, into a host cell, such that the encoded peptide or polypeptide is expressed within the host cell.

The terms "neuroinjury" and "injury" are often used interchangeably herein. "neurotrauma" is one embodiment of a "neuroinjury" and may generally be considered a synonym. A "neuroinjury" is an injury that causes some destruction or death of neurological tissue. A neuroinjury generally has as sequelae some loss, e.g., a diminution of mental, sensory or muscle function.

A "neuroprotectant" is something that can save neurons before they die from the variety of insults presented to them in the acute or semi-acute post-injury phase. After an acute occlusion, there is often a localized area of destroyed brain matter that is surrounded by a penumbral zone that will die within hours if circulation is not restored. The time to death of this penumbral zone can be extended by a few hours in experimental models with "neuroprotectants", such as NMDA antagonists, calcium channel blockers, radical scavengers and trapping agents, anti-apoptotics, caspase inhibitors, parp inhibitors, etc. For this purpose a "neuroprotectant" is something that can save neurons before they die from the variety of insults presented to them in the acute phase By "neuregulin" or "NRG" is meant a polypeptide that is encoded by an NRG-1, NRG-2, NRG-3 or NRG-4 gene or nucleic acid (e.g., a cDNA), and binds to and activates EGFR, ErbB1, ErbB2, ErbB3, or ErbB4 receptors, or combinations thereof.

By "neuregulin-1," "NRG-1," "heregulin," "GGF2," or "p185erbB2 ligand" is meant a polypeptide that binds to the ErbB2 receptor and is encoded by the p185erbB2 ligand gene described in U.S. Pat. No. 5,530,109; U.S. Pat. No. 5,716,930; and U.S. Pat. No. 7,037,888, each of which is incorporated herein by reference in its entirety. Binding to the erbB2 receptor may be indirect through heterologous pairing of the erbB2 receptor to erbB1, erbB3 or erbB4.

By "neuregulin-like polypeptide" is meant a polypeptide that possesses an EGF-like domain encoded by a neuregulin gene, and binds to and activates EGFR, ErbB1, ErbB-2, ErbB-3, ErbB-4, or a combination thereof. Binding to the erbB2 receptor may be indirect through heterologous pairing of the erbB2 receptor to erbB1, erbB3 or erbB4.

As used herein, the term "neurorecovery" is used to refer to the process by which the nervous system restores its functioning towards a normal state following injury, disease, infection or other disruption of the nervous system, the brain, spinal cord or peripheral nerves.

By "operably linked" is meant that a nucleic acid encoding a polypeptide (e.g., a cDNA) and one or more regulatory sequences are connected in such a way as to permit gene expression when the appropriate molecules (e.g., transcriptional activator proteins) are bound to the regulatory sequences.

As used herein "peptide" comprises, consists essentially of, or consists of a peptide of about: 625, 600, 575, 550, 525, 500, 475, 450, 425, 400, 375, 350, 325, 300, 275, 250, 225, 200, 175, 150, 125, 100, 75, 50 or fewer than 50 amino acids.

By "promoter" is meant a minimal sequence sufficient to direct transcription. Also included in the invention are those promoter elements which are sufficient to render promoter-dependent gene expression controllable for cell type or physiological status (e.g., hypoxic versus normoxic conditions), or inducible by external signals or agents; such elements may be located in the 5' or 3' or internal regions of the native gene.

The term "therapeutically effective amount" is intended to mean that amount of a drug or pharmaceutical agent that elicits the biological or medical response of a tissue, a system, animal or human that is being sought by a researcher, veterinarian, medical doctor or other clinician. A therapeutic change is a change in a measured biochemical characteristic in a direction expected to alleviate the disease or condition being addressed. More particularly, a "therapeutically effective amount" is an amount sufficient to decrease the symptoms associated with a medical condition or infirmity, to normalize body functions in disease or disorders that result in impairment of specific bodily functions, or to provide improvement in one or more of the clinically measured parameters of a disease.

As used herein, the term "treating means obtaining recovery following a neuroinjury where there would otherwise be none; accelerating the rate of natural recovery following a neuroinjury; or promoting recovery to a higher functioning level. Without being bound by theory, in the chronic post-injury window it is not contemplated that there will be an ability to lessen any further neurological death, i.e., it is understood in that the nerves have died by the time the chronic window occurs. However, treatment in accordance with the invention comprises during the chronic period, e.g., lessening a decrease function or viability of tissue (e.g., muscle or bone) that would otherwise occur in the tissue served by the comprised nerve. In addition, treatment in accordance with the invention comprises during the chronic period, e.g., lessening of atrophy (e.g., of muscle or bone) that would otherwise occur in the tissue served by the comprised nerve.

By "transformed cell" is meant a cell (or a descendent of a cell) into which a DNA molecule encoding a neuregulin or polypeptide having a neuregulin EGF-like domain has been introduced, by means of recombinant DNA techniques or known gene therapy techniques.

Unless defined otherwise, all technical and scientific terms used herein have the same meaning as commonly understood by one of ordinary skill in the art to which this invention belongs.

BRIEF DESCRIPTION OF THE DRAWINGS

FIGS. 6A-D show the nucleic and amino acid sequences of full length GGF2. The nucleic acid sequence is designated SEQ ID NO: 6 and the amino acid sequence is designated SEQ ID NO: 7. GGF2 variant sequences are identified as follows: GGF-II 09 (SEQ ID NO: 8), GGF-II 08 (SEQ ID NO: 9), GGF-II 04 (SEQ ID NO: 10), GGF-II 01 and 11 (SEQ ID NO: 11), GGF-II 10 (SEQ ID NO: 12), GGF-II 03 (SEQ ID NO: 13), GGF-II 02 (SEQ ID NO: 14), GGF-II 06 (SEQ ID NO: 15), and GGF-II 12 (SEQ ID NO: 16).

FIG. 7 shows the nucleic and amino acid sequences of epidermal growth factor like (EGFL) domain 1. The nucleic acid sequence is designated SEQ ID NO: 17 and the amino acid sequence is designated SEQ ID NO: 18.

FIG. 8 shows the nucleic and amino acid sequences of epidermal growth factor like (EGFL) domain 2. The nucleic acid sequence is designated SEQ ID NO: 19 and the amino acid sequence is designated SEQ ID NO: 20.

FIG. 9 shows the nucleic and amino acid sequences of epidermal growth factor like (EGFL) domain 3. The nucleic acid sequence is designated SEQ ID NO: 21 and the amino acid sequence is designated SEQ ID NO: 22.

FIG. 10 shows the nucleic and amino acid sequences of epidermal growth factor like (EGFL) domain 4. The nucleic acid sequence is designated SEQ ID NO: 23 and the amino acid sequence is designated SEQ ID NO: 24.

FIG. 11 shows the nucleic and amino acid sequences of epidermal growth factor like (EGFL) domain 5. The nucleic acid sequence is designated SEQ ID NO: 25 and the amino acid sequence is designated SEQ ID NO: 26.

FIG. 12 shows the nucleic and amino acid sequences of epidermal growth factor like (EGFL) domain 6. The nucleic acid sequence is designated SEQ ID NO: 27 and the amino acid sequence is designated SEQ ID NO: 28.

FIG. 13 shows the nucleic and amino acid sequences of an epidermal growth factor like peptide from the NRG-1 gene. The nucleic acid sequence is designated SEQ ID NO: 29 and the amino acid sequence is designated SEQ ID NO: 30.

FIG. 14 shows the nucleic and amino acid sequence of an epidermal growth factor like (EGFL) beta fragment from NRG-1 (SEQ ID NO: 31).

FIG. 15 shows the nucleic and amino acid sequence of an epidermal growth factor like (EGFL) alpha fragment from NRG-1 (SEQ ID NO: 32).

FIG. 16 shows the nucleic and amino acid sequence of an epidermal growth factor like (EGFL) alpha fragment from NRG-2 alpha (SEQ ID NO: 33).

FIG. 17 shows the amino acid sequence of an epidermal growth factor like (EGFL) alpha fragment from NRG-2 beta (SEQ ID NO: 34).

FIG. 18 shows amino acid sequence alignments of various EGF-like peptides. EGF-like domain can be defined as sub-domains of NRGs for which sequence alignment reveals at least 25, 26, 27, 28, 29, 30, 31, 32, 33, 34, 35, 36, 37, 38, 39, 40, 41, 42, 43, 44 or 45% homology in amino acid sequence as compared to the human EGF molecule (sequence P01133/971-1023, at the bottom of the alignment in the figure). Homologous amino acids have identical, conserved or semi-conserved physicochemical and structural properties, as denoted by the symbols '*', ':' and '.', respectively. EGF-like domain sequences are identified as follows: Beta2 region (SEQ ID NO: 35), Zensun (SEQ ID NO: 36), 156/416 (SEQ ID NO: 37), RnD (SEQ ID NO: 38), 151 (SEQ ID NO: 39), EGF0-1d_NRGbeta3 (SEQ ID NO: 40), 157/417seq (SEQ ID NO: 41), EGF-1d_GGF (SEQ ID NO: 42), RnD_catno296HR (SEQ ID NO: 43), 155/415_seqid200_seqid155 (SEQ ID NO: 44), EGF-1d_NDF43 (SEQ ID NO: 45), 152 (SEQ ID NO: 46), 159/419 (SEQ ID NO: 47), 158/418 (SEQ ID NO: 48), EGF-1d_NRG1gamma (SEQ ID NO: 49), EGF-1d_GGF2 (SEQ ID NO: 50), EGF-1d_SMDF (SEQ ID NO: 51), 154/414 (SEQ ID NO: 52), P01133/971-1023 (SEQ ID NO: 53).

FIG. 19A shows the expression vector (pSV-AHSG) that CHO (dhfr-) cells were transfected with.

DETAILED DESCRIPTION OF THE INVENTION

As indicated herein, the non-palliative treatment of ischemic stroke has heretofore been confined to therapeutics administered in the acute phase following a stroke.

Immediate cell death due, at least in part, to oxygen deprivation is observed during the acute phase. Furthermore, as shown in FIG. 1, the occlusion of blood flow results in release of intracellular stores of free radicals, glutamate, and calcium and sodium that are understood to destroy brain tissue and expand the area of the lesion.

The semi-acute phase, from approximately six hours to two days (or three days by some definitions) post-neuroinjury, is characterized by continued free radical release, glutamate dumping, calcium and sodium release, oxygen deprivation of the occluded region, and immediate localized cell death. To date, there are no known clinically approved agents for use in humans during the semi-acute phase following a stroke.

Figure 1:
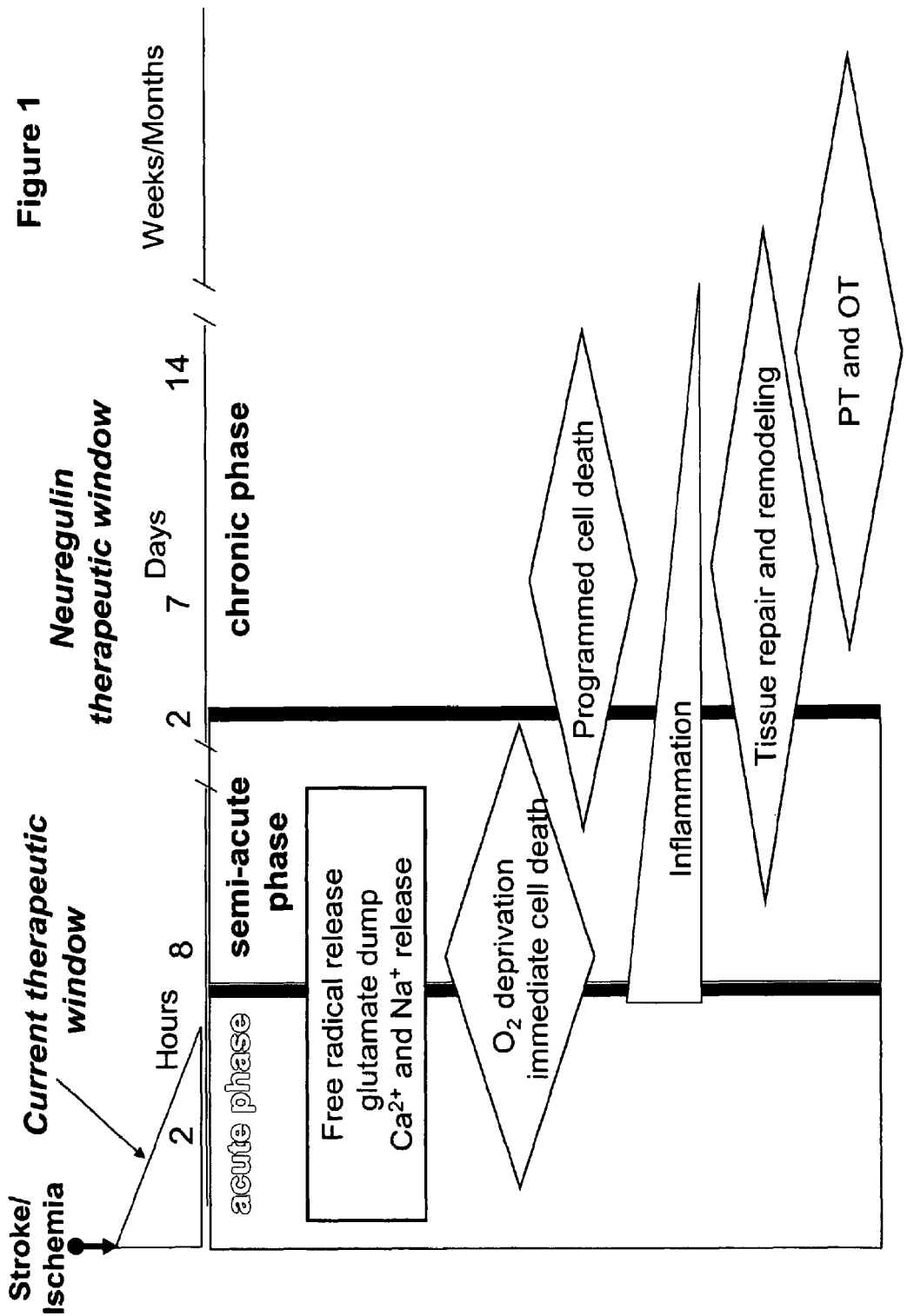
FIG. 1 shows a schematic of the progressive phases following stroke/ischemia. In the figure "OT" indicates occupational therapy and "PT" indicates physical therapy.

As depicted in FIG. 1, the limited window for pharmaceutical post-neuroinjury therapy is at least partially explained by the pathophysiology and temporal progression of the injury. Within minutes, e.g., of an occlusion, neurons at the core of the infarct are destroyed. In the hours after the occlusion, free radicals, excitotoxic and inflammatory agents are released/produced and these molecules continue to destroy brain tissue and expand the area of the lesion. The extent of the injury can be limited, as described above, by restoring blood flow (using a clinically approved clot-buster, i.e., tPA) and thus achieving re-oxygenation of the affected area.

As indicated by the scientific literature, various compounds appear to exhibit efficacy in the acute and semi-acute periods. However, after the 24, 36 or 48 hour marks post-CNS neuroinjury, potential therapies progressively lose the ability to treat the injury. In fact, some of the therapeutics modalities, such as tPA, that have an effect in the acute period begin to have serious, life-threatening contraindications as time occurs post-injury.

Days, weeks or months after an ischemic event, during the chronic phase post-stroke, therapies must be aimed at promoting neurorecovery. The promotion of neurorecovery following a traumatic event such as stroke in the central nervous system involves distinctly different physiologic phenomena and therapeutic strategy than employed in the pre-chronic window. The pre-chronic treatments generally involve agents that aim to restore blood flow and reduce acute cell death. In contrast, a therapeutic agent that can be efficaciously administered at 48 hours or more, or 72 hours or more post-injury is differentiated from acute phase therapeutics by its ability to restore function without altering the size of the ischemic lesion. In one embodiment, treatment in accordance with the invention begins after essentially complete post-injury death of an ischemic CNS lesion; by "essentially complete post-injury death of an ischemic CNS lesion is intended that the CNS cell death that is directly consequent to the ischemic event will have transpired, other cell death due to age or therapy (whether or not the therapy is designed to address the ischemia) is not within the scope of this definition.

As shown herein, the present inventors demonstrated that neuregulins are effective in restoring neurological function during the chronic phase of a neurotraumatic injury. In one embodiment, the neurotraumatic injury is an ischemic stroke. As described herein, the present inventors have made the surprising discovery that neuregulin is effective when dosing is initiated during the chronic phase following an ischemic event. Even more surprising is the discovery that neuregulin is effective even when dosing is initiated as late as 7 days after the ischemic event.

The present data shows that the favorable outcomes achieved have not come about by the same mechanisms found to be effective in immediate post-ischemic treatment. Neuregulin treatment during chronic phase following stroke does not alter the size of the ischemic lesion (see Table 1). This clearly demonstrates that the acute and semi-acute phases of the pathophysiology are complete at these phases, and neuregulin administered during the chronic phase is promoting neurorecovery, rather than establishing reperfusion and protecting neurons.

TABLE 1

| Infarct Volume (%) | |
|---|---|
| bFGF | 21.3 ± 3.3 |
| NRG 1.0 µg/kg | 26.8 ± 3.0 |
| GGF2 6.5 µg/kg | 27.1 ± 3.7 |
| GGF2 100 µg/kg | 26.3 ± 3.5 |
| Vehicle | 25.0 ± 3.5 |

Compositions of the Invention:

As indicated above, neuregulins are polypeptides encoded by the NRG-1, NRG-2, NRG-3 or NRG-4 genes and possess EGF-like domains that allow them to bind to and activate ErbB receptors. Holmes et al. (Science 256:1205-1210, 1992) have shown that the EGF-like domain alone is sufficient to bind and activate the p185erbB2 receptor. Accordingly, any polypeptide product encoded by the NRG-1, NRG-2, NRG-3 or NRG-4 gene, or any neuregulin-like polypeptide, e.g., a polypeptide having an EGF-like domain encoded by a neuregulin gene or cDNA (e.g., an EGF-like domain containing the NRG-1 peptide subdomains C-C/D or C-C/D', as described in U.S. Pat. No. 5,530,109, U.S. Pat. No. 5,716,930, and U.S. Pat. No. 7,037,888; or an EGF-like domain as disclosed in WO 97/09425) may be used in the methods of the invention. A composition of the invention may be in unit dosage form. Kits comprising compositions of the invention and/or instructions in accordance with the invention are within the scope of the present invention as well.

Compositions of the invention may be administered to patients with a pharmaceutically-acceptable diluent, carrier, or excipient. Conventional pharmaceutical practice is employed to provide formulations or compositions to administer such compositions to patients or experimental animals. Although intravenous administration is preferred, any appropriate route of administration may be employed, for example, parenteral, subcutaneous, intramuscular, intracranial, intraorbital, ophthalmic, intraventricular, intracapsular, intraspinal, intracisternal, intraperitoneal, intranasal, aerosol, oral, or transdermal (e.g., by applying an adhesive patch carrying a formulation capable of crossing the dermis and entering the bloodstream) or topical administration.

Therapeutic formulations may be in the form of liquid solutions or suspensions; for oral administration, formulations may be in the form of tablets or capsules; and for intranasal formulations, in the form of powders, nasal drops, or aerosols. Methods well known in the art for making formulations are found in, for example, "Remington's Pharmaceutical Sciences." Formulations for parenteral administration may, for example, contain excipients, sterile water, or saline, polyalkylene glycols such as polyethylene glycol, oils of vegetable origin, or hydrogenated napthalenes. Other potentially useful parenteral delivery systems for administering molecules of the invention include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

As a further aspect of the invention there is provided the present compounds for use as a pharmaceutical especially in the treatment or prevention of the aforementioned conditions and diseases. Also provided herein is the use of the present compounds in the manufacture of a medicament for the treatment or prevention of one of the aforementioned conditions and diseases.

With respect to intravenous injections, dose levels are generally in a range from one value in the following list to a higher value in the list: about 0.001 mg/kg, about 0.01 mg/kg, about 0.1 mg/kg, about 1 mg/kg, and about 10 mg/kg. The dosing periodicity is generally in regular time intervals of from about every 24, 48, 72, or 96 hours. In an alternative embodiment, the dosing periodicity is generally in regular time intervals of from about every 1, 2, 3, 4, 5, 6, 7, days. In an alternative embodiment, the dosing periodicity is generally in regular time intervals of from about every 1, 2, 3, 4, or 5 weeks. After a period of such dosing, less frequent dosing such as monthly, every three months, every four months, or yearly can be employed.

Transdermal doses are selected to provide essentially identical, similar or lower physiologic levels (plasma, tissue, CSF) than are achieved using injection doses.

The compounds of the invention can be administered as the sole active agent or they can be administered in combination with other agents, including other compounds that may be found to demonstrate the same or a similar therapeutic activity and that are determined to be safe and efficacious for such combined administration. Other such compounds contemplated for use in the treatment of acute or semi-acute neuroinjury include hematopoietic factors (e.g., G-CSF and/or GM-CSF); substances that have thrombolytic activities, e.g., tPA, streptokinase, urokinase, and/or Ancrod; antiplatelet agents such as acetylsalicylic acid (aspirin), clopidogrel (Plavix), aspirin combined with extended release dipyridamole (Aggrenox); anticoagulants such as warfarin (Coumadin) or Heparin; and/or substances that interfere with apoptotic signaling (e.g. inhibitors of caspases) or progesterone. It is understood, however, that the above compounds are administered for preventive purposes in advance of stroke (e.g., for antiplatelet agents or anticoagulants), or during the acute phase following stroke (tPA).

In order to evaluate the motor, sensory or cognitive deficits that are effectively treated in accordance with the present invention, several tools are available in the art. Well known indicia for monitoring treatment efficacy include Mini-Mental State Examination (MMSE), Modified Mini-Mental State Examination (3MS), Functional Impairment Measure (FIM, Barthel Test, Fugl-Meyer Motor Score, Wolf Motor Function Test, Jebsen-Taylor hand function test, Nottingham Health Profile Part 1 and Motor Assessment Scale (MAS), Sødring Motor Evaluation Scale (SMES), the Berg Balance Scale (BBS) and Barthel Activities of Daily Living (ADL), and other clinical tests such as measures of affect, speech, swallowing, cognition, motor coordination, strength, sensation and autonomic function, as well as survival rates and hospitalization rates may be used to assess disease progression.

Following injury, disease, infection or other disruption of the nervous system, the brain, spinal cord or peripheral nerves do not function properly due to any combination of gross destruction, apoptosis, disrupted pathways and synapses, inflammation, altered chemical environment, changes in cell metabolism and changes in cellular transcription and translation. As used herein, the term "neurorecovery" is used to refer to the process by which the nervous system restores its functioning towards a normal state. This process may occur by correction, circumvention, reversal or elimination of any of the causes noted above.

Furthermore, it is now believed that significant neurorecovery can occur through a process known as 'plasticity' whereby the nervous system forms new connections to compensate or adapt to other changes. Injuries of the CNS cause disruption of local and long-range connections resulting in disrupted function and disability. Plasticity is an event where new connections are formed between existing neurons. Plasticity has been shown to be a mechanism of neurorecovery in CNS systems including the visual system (Pizzorusso et al.) and the spinal cord (Fawcett J W (2009) Brain 132:1417-1418.). In plasticity, new synapses are formed or existing synapses are strengthened, weakened or removed to allow existing structures and systems to compensate for those that have been destroyed or disrupted in the injury. Other forms of plasticity may include altering the neurochemistry of existing cells to changes the direct synaptic signaling and paracrine signaling. Plasticity may also take the form of altering receptor levels to make neurons and other cells more or less sensitive to direct synaptic or paracrine signaling. These processes are well accepted as mechanism of learning and memory.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention before the priority date of each claim of this application.

While the invention has been described in connection with specific embodiments thereof, it will be understood that it is capable of further modifications and this application is intended to cover any variations, uses, or adaptations of the invention following, in general, the principles of the present invention and including such departures from the present disclosure within known or customary practice within the art to which the invention pertains and may be applied to the essential features hereinbefore set forth, and follows in the scope of the appended claims.

The following Examples will assist those skilled in the art to better understand the invention and its principles and advantages. It is intended that these Examples be illustrative of the invention and not limit the scope thereof.

EXAMPLES

Example 1

Materials and Methods

Animal Preparation:

Fifty (50), adult, male Sprague-Dawley were used for the study (10 extra animals were ordered). All rats were housed and handled for behavioral assessment for seven (7) days prior to surgery for acclimation purposes. At the end of the handling period, rats were randomized and assigned to different groups. Rats were given a unique identification number by tail marking. Ten extra rats were also handled.

Surgical Preparation:

Middle Cerebral Artery Occlusion (MCAO), Tamura Model:

This surgical injury model in the rat is a well accepted model of stroke in the field (Tamura et al, 1981, J Cereb Blood Flow Metab. 1(1):53-60; Tamura et al, 1981, J Cereb Blood Flow Metab. 1(1):61-9). Focal cerebral infarcts were made by permanent occlusion of the proximal right middle cerebral artery (MCA) using a modification of the method of Tamura et al. Male Sprague-Dawley rats (300-400 g at the time of surgery) were anesthetized with 2-3% halothane in the mixture of $N_2O:O_2$ (2:1), and were maintained with 1-1.5% halothane in the mixture of $N_2O:O_2$ (2:1). The temporalis muscle was bisected and reflected through an incision made midway between the eye and the eardrum canal. The proximal MCA was exposed through a subtemporal craniectomy without removing the zygomatic arch and without transecting the facial nerve. The artery was then occluded by microbipolar coagulation from just proximal to the olfactory tract to the inferior cerebral vein, and was transected. Body temperature was maintained at 37.5° C.±0.5° C. throughout the entire procedure. Cefazolin (40 mg/kg; Baxter, Lot 06014.1, Exp. January 2009) was given intraperitoneally (i.p.) one day before MCAO and just after MCAO to prevent infections. Burprenorphine (NDC 12496-0757-1, Lot #700Y02, exp: Jan. 1, 2010) s.c. (0.05-0.1 mg/kg) was given before the MCAO surgery as analgesia.

Compound Preparation and Dosing:

GGF2 and NRG-1 (NRG-EGF):

Stock solutions were prepared at Acorda Therapeutics and stored at 0-5° C. Doses were made up as described below:

Cloning, Expression and Purification of NRG-1 [NRG1b2 EGF Domain (156Q)]

DNA: NRG1b2 egf domain was cloned from human brain cDNA and cloned into pet 15b vector (Novagen cat #69661-3) using NdeI and BamH1 restriction sites. The resulting protein is a 6.92 kda+~3 kDa His tag (=9.35 kDa).

DNA sequence of NRG1b2 egf pet 15 clone

The underlined sequences are the cloning sites (Nde 1 and BamH1)

```
                                          (SEQ ID NO: 1)
CATATGAGCCA TCTTGTAAAA TGTGCGGAGA AGGAGAAAAC

TTTCTGTGTG AATGGAGGGG AGTGCTTCAT GGTGAAAGAC

CTTTCAAACC CCTCGAGATA CTTGTGCAAG TGCCCAAATG

AGTTTACTGG TGATCGCTGC CAAAACTACG TAATGGCCAG

CTTCTACAAG GCGGAGGAGC TGTACCAGTA AGGATCC.
```

The final translated protein from pet15b vector is shown below. The egf domain is underlined.

```
                                          (SEQ ID NO: 2)
         10         20         30         40
MGSSHHHHHH SSGLVPRGSH MSHLVKCAEK EKTFCVNGGE 50         60         70         80
CFMVKDLSNP SRYLCKCPNE FTGDRCQNYV MASFYKAEEL YQ
```

Theoretical pI/Mw: 7.69/9349.58

Protein Expression

The clone was transformed into B121 cells for protein expression using the Overnight Express Autoinduction System (Novagen) in LB media at 25° C. for 24 hours. Expression is primarily in insoluble inclusion bodies.

Protein Refolding: Adapted from Novagen Protein Refolding Kit, 70123-3.

Protein Purification: Protein is loaded onto an anion exchange column DEAE at 2.5 ml/min. The NRG-1 fragment remains in the flow through, whereas the contaminants bind and elute at a higher salt. The loading and washing buffer is 50 mM Tris pH7.9 and elution buffer is 50 mM Tris pH7.9 with 1M NaCl. The flow through is pooled and concentrated with Centriprep YM-3 from Millipore.

Western blotting: Protein expression is assessed by western blotting. Resulting band runs at around 10 kD.

A 4-20% criterion gel (Biorad) was used for protein resolution followed by transfer onto Protran nitrocellulose paper (0.1 μm pore size from Schliecher and Schull). The blot is blocked in 5% milk in TBS-T (0.1%). Primary antibody (Anti EGF Human NRG1-alpha/HRG1-alpha Affinity Purified Polyclonal Ab Cat # AF-296-NA from R&D systems) 1:1000 dilution in 5% milk in TBS-T-1 hour at RT (also works at 4° C. overnight). Rabbit anti goat HRP secondary antibody was used at 1:10,000 dilution in 5% milk in TBS-T for 1 hour at RT. All washes were performed in TBS-T.

Purification Protocol for NRG-1

The cultures are grown at 25° C. in Overnight Express Autoinduction System 1 from Novagen (cat#71300-4). There is very little soluble NRG-1 present. The culture is spun down and the pellets are extracted, solubilized and re-folded to acquire the NRG-1 before purification can take place.

Materials for Extraction, Solubilization and Re-Folding:

10× Wash Buffer: 200 mM Tris-HCl, pH 7.5, 100 mM EDTA, 10% Triton X-100

10× Solubilization Buffer: 500 mM CAPS, pH 11.0

50× Dialysis Buffer: 1M Tris-HCl, pH 8.5

30% N-laurylsarcosine—add as powder (Sigma 61739-5G)

1M DTT

Reduced glutathione (Novagen 3541)

Oxidized glutathione (Novagen 3542)

A. Cell Lysis and Preparation of Inclusion Bodies

Thaw and re-suspend cell pellet in 30 mls 1× wash buffer. Mix as needed for full re-suspension.

Add protease inhibitors (25 ul of 10× per 50 mls), DNase (200 ul of 1 mg/ml per 50 ml) and MgCl2 (500 ul of 1M per 50 mls) to suspension.

Lyse the cells by sonication.

a. Cool the cells on ice throughout this step.

b. Using the square tip, sonicate for 30 seconds on level 6, 10 times until suspension become less viscous. Let suspension cool on ice for 60 seconds between each sonication. Keep volume no higher than 40 mls in 50 ml conical tube when sonicating.

When complete, transfer each suspension to 250 ml angled neck centrifuge bottles for use with F-16/250 rotor.

Collect the inclusion bodies by centrifugation at 10000×g for 12 minutes.

Remove the supernatant (save a sample for analysis of soluble protein) and thoroughly re-suspend the pellet in 30 mls of 1× Wash Buffer.

Repeat centrifugation as in Step 4 and save the pellet.

Again, thoroughly re-suspend the pellet in 30 mls of 1× Wash Buffer.

Collect the inclusion bodies by centrifugation at 10000×g for 10 minutes. Decant the supernatant and remove the last traces of liquid by tapping the inverted tube on a paper towel.

B. Solubilization and Refolding

From the wet weight of inclusion bodies to be processed, calculate the amount of 1× Solubilization Buffer necessary to re-suspend the inclusion bodies at a concentration of 10-15 mg/ml. If the calculated volume is greater than 250 ml, use 250 ml.

At room temperature, prepare the calculated volume of 1× Solubilization Buffer supplemented with 0.3% N-laurylsarcosine (up to 2% may be used if needed in further optimization) (300 mg/100 mL buffer) and 1 mM DTT.

Add the calculated amount of 1× Solubilization Buffer from step 2 to the inclusion bodies and gently mix. Large debris can be broken up by repeated pipetting.

Incubate in refrigerator shaker at 25° C., 50-100 rpm for 4-5 hours.

Clarify by centrifugation at 10000×g for 10 minutes at room temperature.

C. Dialysis Protocol for Protein Refolding

Prepare the required volume of buffer for dialysis of solubilized protein. The dialysis should be performed with at least 2 buffer changes of greater than 50 times the volume of the sample.

Dilute the 50× Dialysis Buffer to 1× at the desired volume and supplement with 0.1 mM DTT.

Dialyze for at least 4 hours at 4° C. Change the buffer and continue. Dialyze for an additional 4 or more hours.

Prepare additional dialysis buffer as determined in step 1, but omit DTT.

Continue the dialysis through two additional changes (min. 4 hr each), with the dialysis buffer lacking DTT.

D. Redox Refolding Buffer to Promote Disulfide Bond Formation

Prepare a dialysis buffer containing 1 mM reduced glutathione (1.2 g/4 L) and 0.2 mM oxidized glutathione (0.48 g/4 L) in 1× Dialysis Buffer. The volume should be 25 times greater than the volume of the solubilized protein sample. Chill to 4° C.

Dialyze the refolded protein from step 1 overnight at 4° C.

Purification

All procedures are done at 4° C.

Chemicals:

Trizma Hydrochloride (Sigma T5941-500G)

Sodium Chloride 5M Solution (Sigma S6546-4L)

Sodium Hydroxide 10N (JT Baker 5674-02)

E. Purification on the DEAE HiPrep 16/10 Anion Column—20 mls (GE Healthcare)

Buffer A: 50 mM Tris-HCL pH8.0

Buffer B: 50 mM Tris-HCL with 1M NaCl pH 8.0

Equilibration of column: Buffer A—5CV, Buffer B-5CV, Buffer A—10CV

Load 50 ml of sample per run on 20 ml column at 2.0 ml/min (NRG-1) is in the flow through).

Wash 20 ml column with 5CV of buffer A 20 ml column with gradient to 100% B with 5CV. This is to elute off contaminants.

Clean with 10CV of 100% Buffer B.

Equilibrate with 15CV of Buffer A

Analyze fractions with a SDS-page silver stain

Pool fractions with NRG-1 (10 kDa)

F. Concentration of NRG-1

Concentrate with Millipore Centriprep 3000 MWCO 15 ml concentrator (Ultracel YM-3, 4320)

Use Modified Lowry Protein Assay to determine concentration.

G. His-Tag Removal

Removal of the His-Tag is done with A Thrombin Cleavage Capture Kit from Novagen (Cat#69022-3). Based on previous testing the best conditions are room temp for 4 hours with Thrombin at 0.005 U of enzyme per 0 for every 10 μg of NRG-1 protein. After four hours of incubation, add 16 μl of Streptavidin Agarose slurry per unit of Thrombin enzyme. Rock sample for 30 min at room temp. Recover the NRG-1 through spin-filtration or sterile filtering (depending on volume). Complete cleavage is determined with an EGF and Anti-His western.

H. Storage in Final Buffer

Stored in 1×PBS with 0.2% BSA at 4° C.

Expression and Purification of GGF2

For the cloning and background information for GGF2, see U.S. Pat. No. 5,530,109. The cell line is described in U.S. Pat. No. 6,051,401. The entire content of each of U.S. Pat. No. 5,530,109 and U.S. Pat. No. 6,051,401 is incorporated herein by reference in its entirety.

CHO-(Alpha2HSG)-GGF cell line: This cell line was designed to produce sufficient quantities of fetuin (human alpha 2HSG) to support high production rates of rhGGF2 in serum free conditions.

Figure 19A:
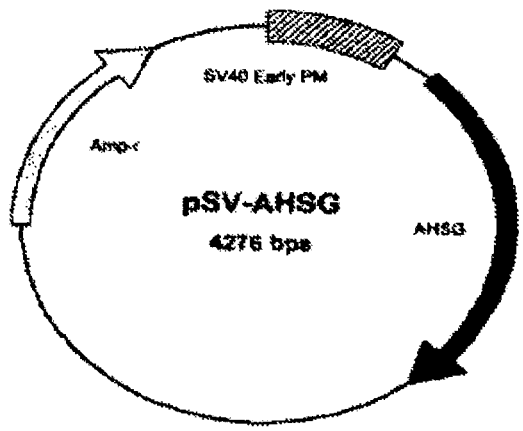
Figure 19B:
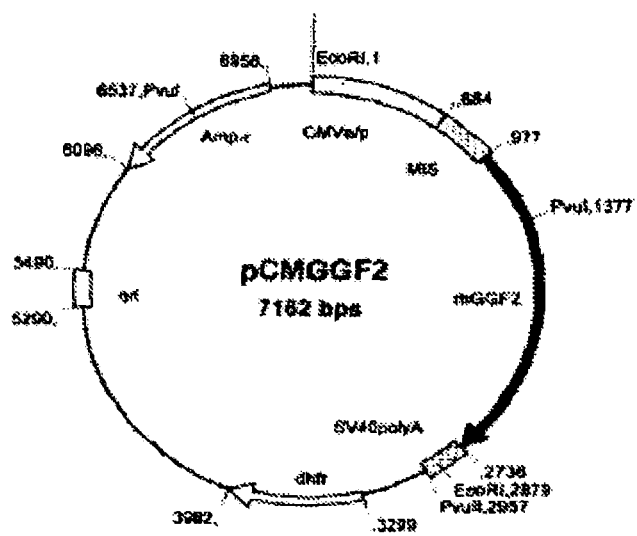
FIG. 19B shows the pCMGGF2 vector containing the coding sequence for human GGF2 that the dhfr−/α2HSGP cells were transfected with using the cationic lipid DMRIE-C reagent (Life Technologies #10459-014)

Cho (dhfr-) cells were transfected with the expression vector fpSV-AHSG) shown in FIG. 19A. Stable cells were grown under ampicillin pressure. The cell line was designated (dhfr⁻/α2HSGP). The dhfr⁻/α2HSGP cells were then transfected with the pCMGGF2 vector shown in FIG. 19B containing the coding sequence for human GGF2 using the cationic lipid DMRIE-C reagent (Life Technologies #10459-014) (See FIGS. 19A-19B).

Stable and high producing cell lines were derived under standard protocols using methotrexate (100 nM, 200 nM, 400 nM, 1 μM) at 4-6 weeks intervals. The cells were gradually weaned from serum containing media. Clones were isolated by standard limiting dilution methodologies. Details of the media requirements are found in the above mentioned reports.

Figure 19C:
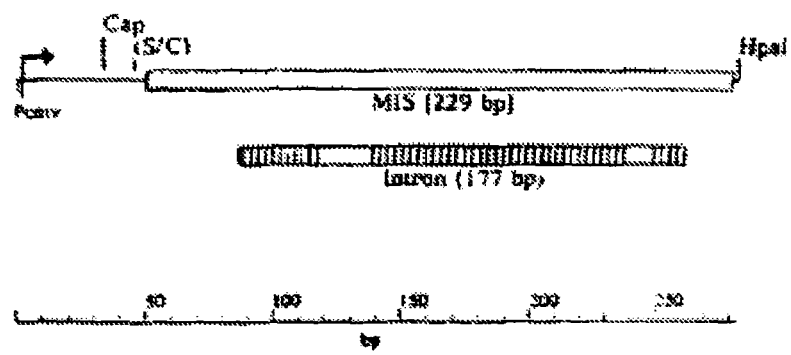
FIG. 19C shows the GGF2 coding sequence placed after the EBV BMLF-1 intervening sequence (MIS).

To enhance transcription, the GGF2 coding sequence was placed after the EBV BMLF-1 intervening sequence (MIS). See FIG. 19C.

(SEQ ID NO: 3)

"MIS Sequence
CGAT[AACTAGCAGCATTTCCTCCAACGAGGATCCCGCAG(GTAAGAAG

CTACACCGGCCAGTGGCCGGGGCCCGATAACTAGCAGCATTTCCTCCAA

CGAGGATCCCGCAG(GTAAGAAGCTACACCGGCCAGTGGCCGGGGCC

GTGGAGCCGGGGCATCCGGTGCCTGAGACAGAGGTGCTCAAGGCAGTC

TCCACCTTTTGTCTCCCCTCTGCAG)AGAGCCACATTCTGGAA]GTT

GGF2 Protein Sequence (SEQ ID NO: 4).

```
        atgagatgg cgacgcgccc cgcgccgctc cgggcgtccc
301 ggccccggg cccagcgccc cggctccgcc gcccgctcgt cgccgccgct gccgctgctg
361 ccactactgc tgctgctggg gaccgcggcc ctggcgccgg gggcggcggc cggcaacgag
421 gcggctcccg cgggggcctc ggtgtgctac tcgtccccgc ccagcgtggg atcggtgcag
481 gagctagctc agcgcgccgc ggtggtgatc gagggaaagg tgcacccgca gcggcggcag
541 caggggcac tcgacaggaa ggcggcggcg gcggcggcg aggcaggggc gtgggcggc
601 gatcgcgagc cgccagccgc gggcccacgg gcgctggggc cgccgccga ggagccgctg
661 ctcgccgcca acgggaccgt gccctcttgg cccaccgccc cggtgcccag cgccggcgag
721 cccggggagg aggcgcccta tctggtgaag gtgcaccagg tgtgggcggt gaaagccggg
781 ggcttgaaga aggactcgct gctcaccgtg cgcctgggga cctggggcca ccccgccttc
841 ccctcctgcg ggaggctcaa ggaggacagc aggtacatct tcttcatgga gcccgacgcc
901 aacagcacca gccgcgcgcc ggccgccttc cgagcctctt tccccctct ggagacgggc
961 cggaacctca agaggaggt cagccgggtg ctgtgcaagc ggtgcgcctt gcctccccaa
1021 ttgaaagaga tgaaagcca ggaatcggct gcaggttcca aactagtcct tcggtgtgaa
1081 accagttctg aatactcctc tctcagattc aagtggttca agaatgggaa tgaattgaat
1141 cgaaaaaaca accacaaaa tatcaagata caaaaaaagc cagggaagtc agaacttcgc
1201 attaacaaag catcactggc tgattctgga gagtatatgt gcaaagtgat cagcaaatta
```

```
1261 ggaaatgaca gtgcctctgc caatatcacc atcgtggaat caaacgctac atctacatcc 1321 accactggga caagccatct tgtaaaatgt gcggagaagg agaaaacttt ctgtgtgaat 1381 ggaggggagt gcttcatggt gaaagacctt tcaaacccct cgagatactt gtgcaagtgc 1441 ccaaatgagt ttactggtga tcgctgccaa aactacgtaa tggccagctt ctacagtacg 1501 tccactccct ttctgtctct gcctgaatag
```

GGF2 Protein Sequences (SEQ ID NO: 5.)

MRWRRAPRRSGRPGPRAQRPGSAARSSPPLPLLPL
LLLLGTAALAPGAAAGNEAAPAGASVCYSSPPSVGSVQELAQRAAVVIE
GKVHPQRRQQGALDRKAAAAAGEAGAWGGDREPPAAGPRALGPPAEEPL
LAANGTVPSWPTAPVPSAGEPGEEAPYLVKVHQVWAVKAGGLKKDSLLT
VRLGTWGHPAFPSCGRLKEDSRYIFFMEPDANSTSRAPAAFRASFPPLE
TGRNLKKEVSRVLCKRCALPPQLKEMKSQESAAGSKLVLRCETSSEYSS
LRFKWFKNGNELNRKNKPQNIKIQKKPGKSELRINKASLADSGEYMCKV
ISKLGNDSASANITIVESNATSTSTTGTSHLVKCAEKEKTFCVNGGECF
MVKDLSNPSRYLCKCPNEFTGDRCQNYVMASFYSTSTPFLSLPE

GGF2 production: One vial of GGF2 at $2.2 \times 10^6$ cells/mL was thawed into 100 mls of Acorda Medium 1 (see Table 2) and expanded until reaching sufficient numbers to seed production vessels. Cells were inoculated into the production media Acorda Medium 2 (see Table 3) at $1.0 \times 10^5$ cells/mL in two liter vented roller bottles. Roller bottles are maintained at 37° C. for 5 days and then reduced to 27° C. for 26 days. The roller bottles are monitored for cell count and general appearance but they are not fed. Once viability is below 10% the cells are spun out and conditioned media harvested and sterile filtered.

TABLE 2

Medium 1

| Item | Vendor | Catalog Number | Final concentration |
|---|---|---|---|
| CD-CHO | Invitrogen | 10743-029 | -remove 50 ml, then add components below |
| $FeSO_4 \cdot EDTA$ | Sigma | F-0518 | 1x (10 ml/L) |
| L-Glutamine | Cellgro | 25-005-CI | 4 mM (20 ml/L) |
| Recombinant Human Insulin | Sigma | I-9278 | 290 U/L (1 ml/L) |
| Non-essential amino acid | Cellgro | 25-025-CI | 1x (10 ml/L) |
| Peptone Type 4 Soybean-HySoy | Sigma | P0521 | Powder - Made 20X in CD-CHO (50 ml/L) |
| Gentamicin | Invitrogen | 15750-078 | 100 μg (2 ml/L) |

TABLE 3

Medium 2

| Item | Vendor | Catalog Number | Final concentration |
|---|---|---|---|
| CD-CHO | Invitrogen | 10743-029 | 50% (~50 ml first) |
| HyQ SFX-CHO | HyClone | SH30187.02 | 50% (~50 ml first) |
| $FeSO_4 \cdot EDTA$ | Sigma | F-0518 | 1x (10 ml/L) |
| L-Glutamine | Cellgro | 25-005-CI | 4 mM (20 ml/L) |

TABLE 3-continued

Medium 2

| Item | Vendor | Catalog Number | Final concentration |
|---|---|---|---|
| Recombinant Human Insulin | Sigma | I-9278 | 290 U/L (1 ml/L) |
| Non-essential amino acid | Cellgro | 25-025-CI | 1x (10 ml/L) |
| Peptone Type 4 Soybean-HySoy | Sigma | P0521 | Powder - Made 20X in CD-CHO (50 ml/L) |
| Gentamicin | Invitrogen | 15750-078 | 100 μg (2 ml/L) |

Purification Protocol for GGF2
All procedures are done at 4° C.
Chemicals:
Sodium Acetate
Glacial Acetic Acid (for pH adjustment)
10N NaOH (for pH adjustment)
NaCl
Sodium Sulfate
L-Arginine (JT Baker cat #: 2066-06)
Mannitol (JT Baker cat #: 2553-01)
Starting material: Conditioned media supernatant. Adjust pH to 6.5.
Step 1:
Capture—Cation Exchange Chromatography
HiPrep SP 16/10 (Amersham Biosciences)
Column equilibration: Buffer A—5CV, buffer B—5CV, buffer 15% B—5CV
Buffer A: 20 mM NaAcetate, pH 6.0
Buffer B: 20 mM NaAcetate, pH 6.0, 1M NaCl
Load sample at 2 ml/min with a continuous load overnight if possible. Binding is better with continuous loading.
Maximum capacity for a starting sample: 5 mg GGF2/ml media
Flow rate: 3 ml/min
First wash: 15% B, 10CV
Second wash: 35% B, 10CV
GGF2 elution: 60% B, 8CV
Column wash: 100% B, 8CV

| Buffers: | Composition | Conductivity | Use |
|---|---|---|---|
| 15% B | 20 mM NaAcetate, pH 6.0, 150 mM NaCl | | First wash |
| | Preequilibration | | |
| 35% B | 20 mM NaAcetate, pH 6.0, 350 mM NaCl | | Second wash |
| 60% B | 20 mM NaAcetate, pH 6.0, 600 mM NaCl | | GGF2 elution |
| 100% B | 20 mM NaAcetate, pH 6.0, 1000 mM NaCl | 88 mS/cm | Column wash |

Step 2:
Refinement—Gel Filtration Chromatography
Sephacryl S200 26/60
Elution buffer: 20 mM NaAcetate, 100 mM Sodium Sulfate, 1% mannitol, 10 mM L-Arginine, pH 6.5
Buffer conductivity:
Sample: SP GGF2 elution pool concentrated up to ~AU280 1.0
Flow rate: 1.3 ml/min
Peak elution: at ~0.36CV from injection start
Step 3:
DNA and Endotoxin Removal—Filtration Through Intercept Q Membrane.
Preequilibration buffer: 20 mM NaAcetate, 100 mM Sodium Sulfate, 1% Mannitol,
10 mM L-Arginine, pH 6.5
Collect flow through
Step 4:
Final Formulation and Sample Preparation
Add additional 90 mM L-Arginine to the sample
Concentrate
Sterile Filter The vehicle/control article used herein is 0.2% Bovine Serum Albumin (BSA), 0.1M Sodium Phosphate, pH 7.6 or 0.1M sodium phosphate, pH 7.6 as indicated.

Basic FGF:

The bFGF (PeproTech Inc., 100-18B, Lot 1206CY08 G2407) was reconstituted as directed by PeproTech to a stock solution of 0.1 mg/ml and stored at −20° C. before use. On the day of the injection, 100 µg/ml of BSA (Roche Diagnostics, Lot 12403328 exp. Mar. 31, 2008) solution was made as diluent, to make a final bFGF concentration of 20 µg/ml (1 µg/50 ul). This material was only used in study 1.

Randomization and Blinding: Five animals were operated on per day. The investigator doing the surgery and behavioral assessments was blinded to treatment assignment of each animal (except the bFGF treated group) until all of the data were collected.

Behavioral Tests:

Sensorimotor functional activities were evaluated using forelimb and hindlimb placing, and body swing behavioral tests. These tests were performed one (1) day before surgery, one (1) day after surgery and at three (3), seven (7), fourteen (14) and twenty-one (21) days after MCAO.

1. Limb Placing

Limb placing tests were divided into both forelimb and hindlimb tests. For the forelimb placing test, the examiner held the rat close to a tabletop and scored the rat's ability to place the forelimb on the tabletop in response to whisker, visual, tactile, or proprioceptive stimulation. Similarly, for the hindlimb placing test, the examiner assessed the rat's ability to place the hindlimb on the tabletop in response to tactile and proprioceptive stimulation. Separate sub-scores were obtained for each mode of sensory input (halfpoint designations possible), and added to give total scores (for the forelimb placing test: 0=normal, 12=maximally impaired; for the hindlimb placing test: 0=normal; 6=maximally impaired).

2. Body Swing Test

The rat was held approximately one inch from the base of its tail. It was then elevated to an inch above a surface of a table. The rat was held in the vertical axis, defined as no more than 10° to either the left or the right side. A swing was recorded whenever the rat moved its head out of the vertical axis to either side. The rat must return to the vertical position for the next swing to be counted. Thirty (30) total swings were counted. A normal rat typically has an equal number of swings to either side. Following focal ischemia, the rat tends to swing to the contralateral (left) side.

On all the days of the behavioral tests, animals were tested before drug administration. Time points are designated with the day of surgery (Day 0) as a reference.

Sacrifice and Infarct Volume:

Following behavioral evaluations at twenty one (21) days after MCAO, rats were deeply anesthetized with Ketamine (50-100 mg/kg) and Xylazine (5-10 mg/kg) mixture, intraperitoneally. Animals were perfused transcardially with normal saline (with heparin, 2 unit/ml) followed by 10% formalin. Brains were then removed and stored in 10% formalin. Fixed brains were then embedded with paraffin, and 5 micron coronal sections were cut using a microtome. Sections were then stained with hematoxylin and eosin (H&E). Seven sections (+4.7, +2.7, +0.7, −1.3, −3.3, −5.3 and −7.3, compared to bregma respectively) from each brain were photographed by a digital camera, and the infarct area on each slice was determined by NIH Image (Image J) using the "indirect method" (area of the intact contralateral [left] hemisphere—area of intact regions of the ipsilateral [right] hemisphere) to correct for brain edema. Infarct areas were then summed among slices and multiplied by slice thickness to give total infarct volume, which was expressed as a percentage of intact contralateral hemispheric volume.

Example 2

Effect of GGF2 (an NRG-1) in Enhancing Neurological Recovery in a Model of Permanent Middle Cerebral Artery Occlusion (MCAO) in Rats—Treatment Initiated During the Acute Phase and Continuing Thereafter Effects of GGF2 and NRG-1: Functional Recovery Following MCA Occlusion (MCAO) in Rats Study 1 Experimental groups (n=10):

NRG-1, 1.0 µg/kg, 1 ml/kg intravenous; 1 hr after, & once per day (q24) for 10 days after MCAO GGF2, 6.5 µg/kg, 1 ml/kg intravenous; 1 hr after, & q24 for 10 days after MCAO GGF2, 100 µg/kg, 1 ml/kg intravenous; 1 hr after, & q24 for 10 days after MCAO bFGF, intracisternal, 1 µg/50 µl; Day 1 and Day 3 (positive control) after MCAO Vehicle, 1 ml/kg intravenous; 1 hr after, & q24 for 10 days after MCAO (Vehicle=0.2% BSA/0.1M sodium phosphate pH 7.6)

All data are expressed as mean±S.E.M. Behavioral and body weight data were analyzed by repeated measures of ANOVA (treatment X time), unless otherwise specified. Positive F-values for overall ANOVAs including all groups enabled pairwise ANOVAs between groups. Infarct volume data were analyzed by one-way ANOVA.

Figure 2:
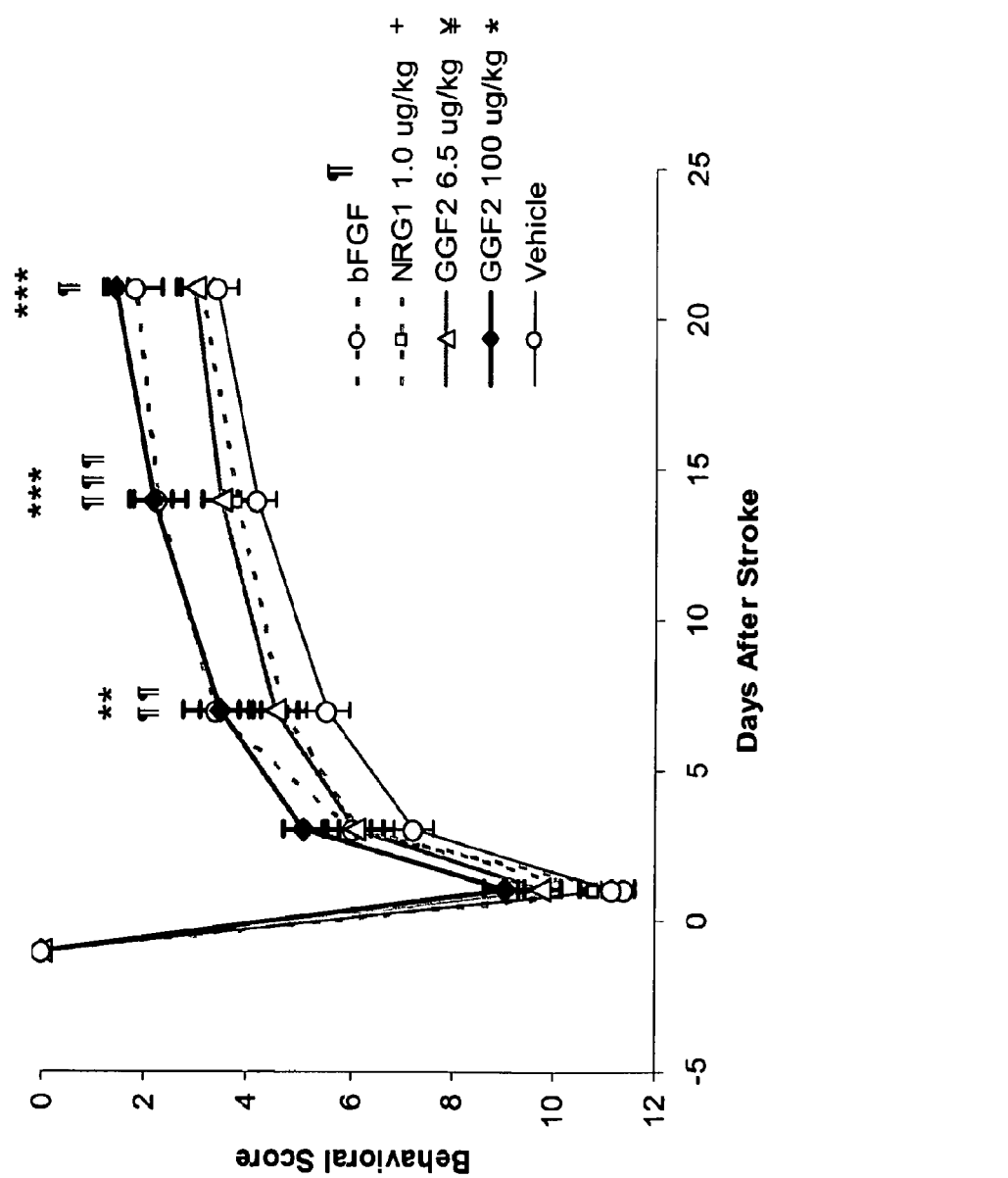
FIG. 2 depicts forelimb behavioral scores following permanent ligation of the middle cerebral artery. Rats were treated with GGF2, NRG1, FGF, or vehicle as indicated. FGF and GGF2 at 100 µg/kg demonstrated significant improvements at the Day 21 behavioral test. (¶, +, ¥, * indicate significantly different from vehicle for bFGF, NRG1, GGF2 at 6.5 ug/kg and GGF2 at 100 ug/kg by ANOVA and post-Tukey).

Results:

Forelimb Placing Test:

Recovery in the GGF2, 100 µg/kg group was superior to the vehicle group (p<0.001). Recovery in the bFGF group was superior to the vehicle group (p<0.05). There was no significant difference in recovery of the GGF2, 6.5 µg/kg or NRG, 1.0 µg/kg groups compared to the vehicle group. See FIG. 2.

Figure 3:
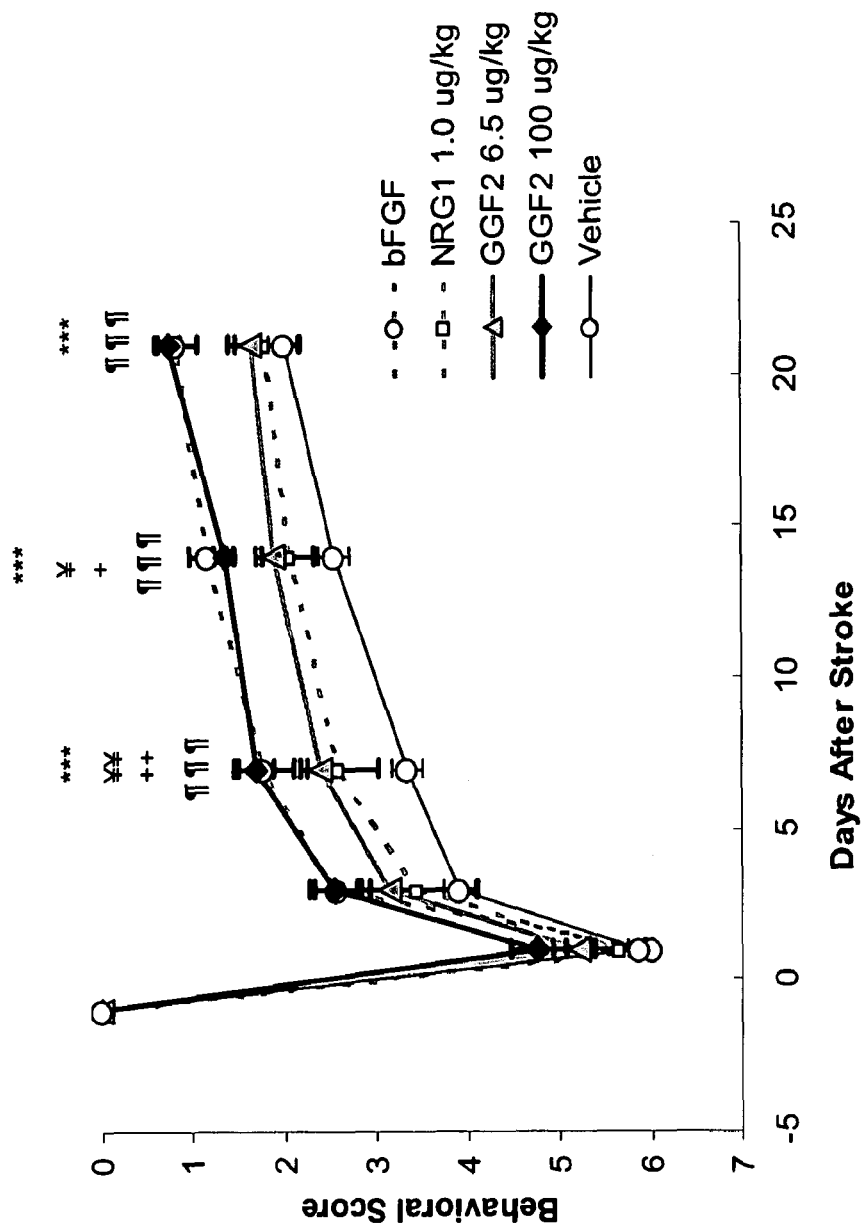
FIG. 3 depicts hindlimb behavioral scores following permanent ligation of the middle cerebral artery. Rats were treated with GGF2, NRG1, FGF, or vehicle as indicated. GGF2 at 6.5 µg/kg and NRG at 1.0 µg/kg were significantly better than vehicle at the Day 7 and 14 behavioral testing, but not at the study endpoint on Day 21. GGF2 at 100 µg/kg and FGF were significantly better than vehicle at all behavioral time points after treatment. (¶, +, ¥, * indicate significantly different from vehicle for bFGF, NRG1, GGF2 at 6.5 ug/kg and GGF2 at 100 ug/kg by ANOVA and post-Tukey).

Hindlimb Placing Test:

Recovery in the bFGF and GGF2, 100 µg/kg group was significantly better than the vehicle group (p<0.001) on all behavioral testing days. Recovery in the GGF2, 6.5 µg/kg group and NRG, 1.0 µg/kg group was significantly improved compared to vehicle on behavioral testing Days 7 and 14 but this effect was not maintained to the 21 day end point. See FIG. 3.

Figure 4:
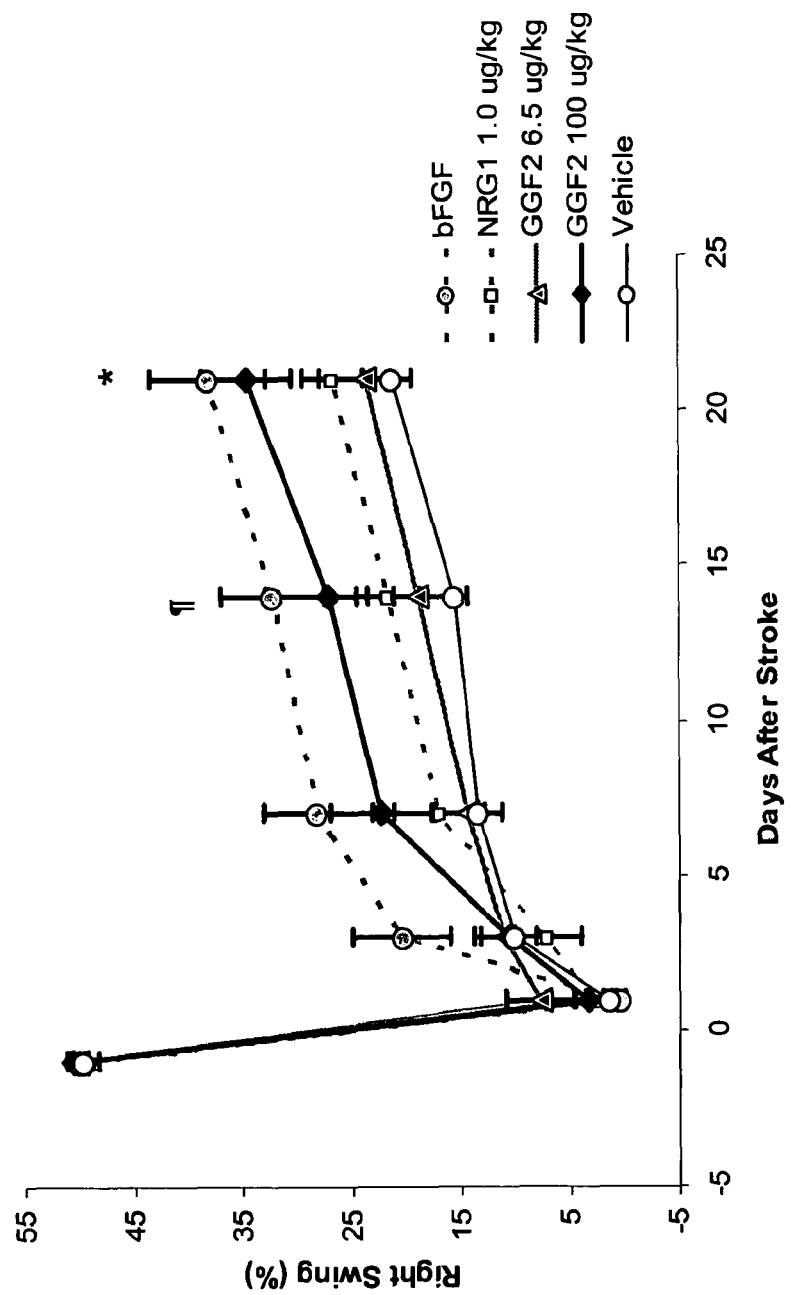
FIG. 4 depicts body swing behavioral scores following permanent ligation of the middle cerebral artery. Rats were treated with GGF2, NRG1, FGF, or vehicle as indicated. GGF2 at 100 µg/kg and FGF were significantly improved compared to vehicle at Day 21. (¶, +, ¥, * indicate significantly different from vehicle for bFGF, NRG1, GGF2 at 6.5 ug/kg and GGF2 at 100 ug/kg by repeated measures ANOVA and post-hoc Tukey).

Body Swing Test:

Recovery in the bFGF group and GGF2, 100 µg/kg group was significantly improved compared to vehicle (p<0.05) at the behavioral testing Day 21 end point. There was no significant difference in recovery of the NRG, 1.0 µg/kg group, or the GGF2, 6.5 µg/kg group compared to the vehicle group. See FIG. 4.

Weight Changes:

There were no significant differences among the groups.

Infarct Volume There were no significant differences among the groups. See Table 1 above.

Summary:

These results demonstrate that GGF2 is acting in a dose responsive manner and promotes functional recovery in this model of permanent stroke. The hindlimb data using the lower dose of neuregulin shows that continued treatment can lead to continued improvements.

Example 3

Effect of Timing of Administration (Post-Injury Delay) of Dosing of GGF2 in Enhancing Neurological Recovery in a Permanent Middle Cerebral Artery Occlusion (MCAO) in Rats Including Chronic Period Dosing Effects of GGF2 on Functional Recovery Following MCAO in Rats Experimental groups (n=10):

GGF2, 0.1 mg/kg, (1 ml/kg) intravenous; 10 daily injections, starting at Day 1 after MCAO GGF2, 0.1 mg/kg, (1 ml/kg) intravenous; 10 daily injections, starting at Day 3 after MCAO GGF2, 0.1 mg/kg, (1 ml/kg) intravenous; 10 daily injections, starting at Day 7 after MCAO Vehicle, 1 ml/kg intravenous; 10 daily injections, starting at Day 1 after MCAO (Vehicle=0.1M sodium phosphate pH 7.6)

Animals start to receive GGF2 or vehicle intravenously at Day 1, Day 3 or Day 7 for 10 days after MCAO. All solutions were made fresh every day.

Figure 5A:
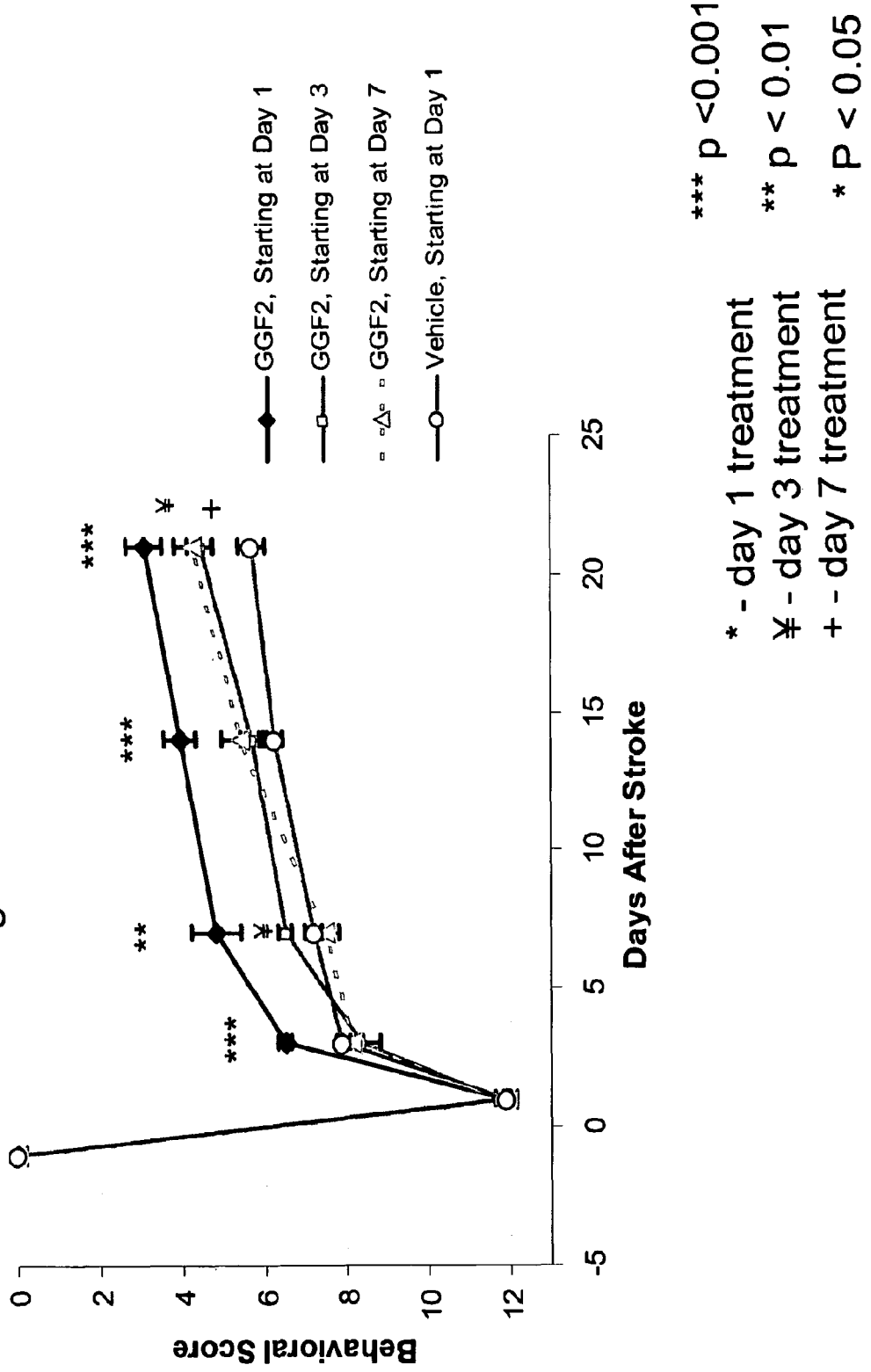
FIG. 5A shows forelimb behavioral scores following permanent ligation of the middle cerebral artery. Rats were treated with GGF2 starting 1, 3 or 7 days after the ligation. GGF2 was delivered at 0.1 mg/kg, IV daily for 10 days. Forelimb behavioral scores were significantly better than vehicle with all treatment paradigms at the day 21 time point. (*, ¥, + indicate significantly different from vehicle for the day 1, 3 and 7 treatment groups, respectively by repeated measures ANOVA and post-hoc Tukey).

Results:

Forelimb Placing:

Recovery in the Day 1 GGF2 treatment group significantly improved compared to the vehicle group at all time points of testing after treatment (on Day 3 (p<0.0001), on Day 7 (p<0.005), on Day 14 (p<0.0001) and on Day 21 (p<0.0001)). The Day 3 GGF2 treatment group demonstrated significant improvements compared to vehicle on day 7 (p<0.05) and day 21 (p<0.05) The Day 7 GGF2 treatment group demonstrated a clear deflection in the slope of recovery compared to vehicle from Day 7 (start of treatment) to Day 14, this difference became significant by Day 21 (p<0.05). These data indicated that treatment as late as three and even 7 days after injury can produce significant improvements in neurological function. More prolonged treatment may be beneficial and result in greater and more sustained effects. See FIG. 5A.

Figure 5B:
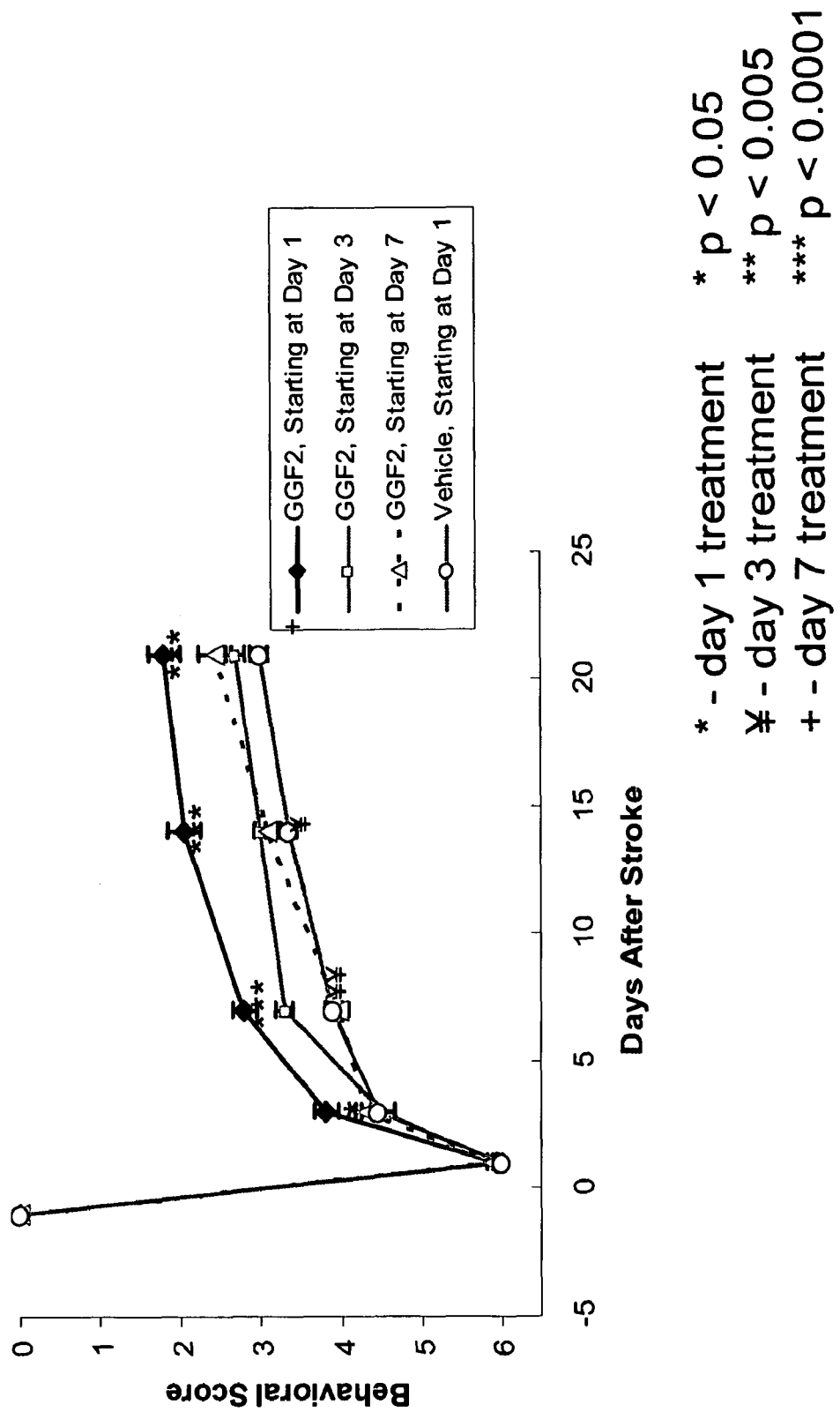
FIG. 5B shows hindlimb behavioral scores following permanent ligation of the middle cerebral artery. Rats were treated with GGF2 starting 1, 3 or 7 days after the ligation. GGF2 was delivered at 0.1 mg/kg, IV daily for 10 days. Hindlimb behavioral scores were significantly better than vehicle when treatment was initiated at 1 or 7 days after ligation, and were improved compared to vehicle with treatment initiated 3 days post ligation at the day 21 time point. (*, ¥, + indicate significantly different from vehicle for the day 1, 3 and 7 treatment groups, respectively by repeated measures ANOVA and post-hoc Tukey).

Hindlimb Placing:

Recovery in the Day 1 GGF2 treatment group was significantly improved compared to the vehicle group at all time points of testing after treatment (on Day 3 (p<0.05) and on Days 7, 14 and 21 (p<0.0001)). The Day 3 GGF2 treatment group demonstrated improvements that were significantly better than vehicle on testing Day 7 (p<0.001) and Day 14 (p<0.05, day after treatment ended), and were trending toward significance on Day 21 (p<0.065). The Day 7 GGF2 treatment group was significantly improved compared to vehicle at the testing Day 21 end point of the study (p<0.05). FIG. 5B.

Figure 5C:
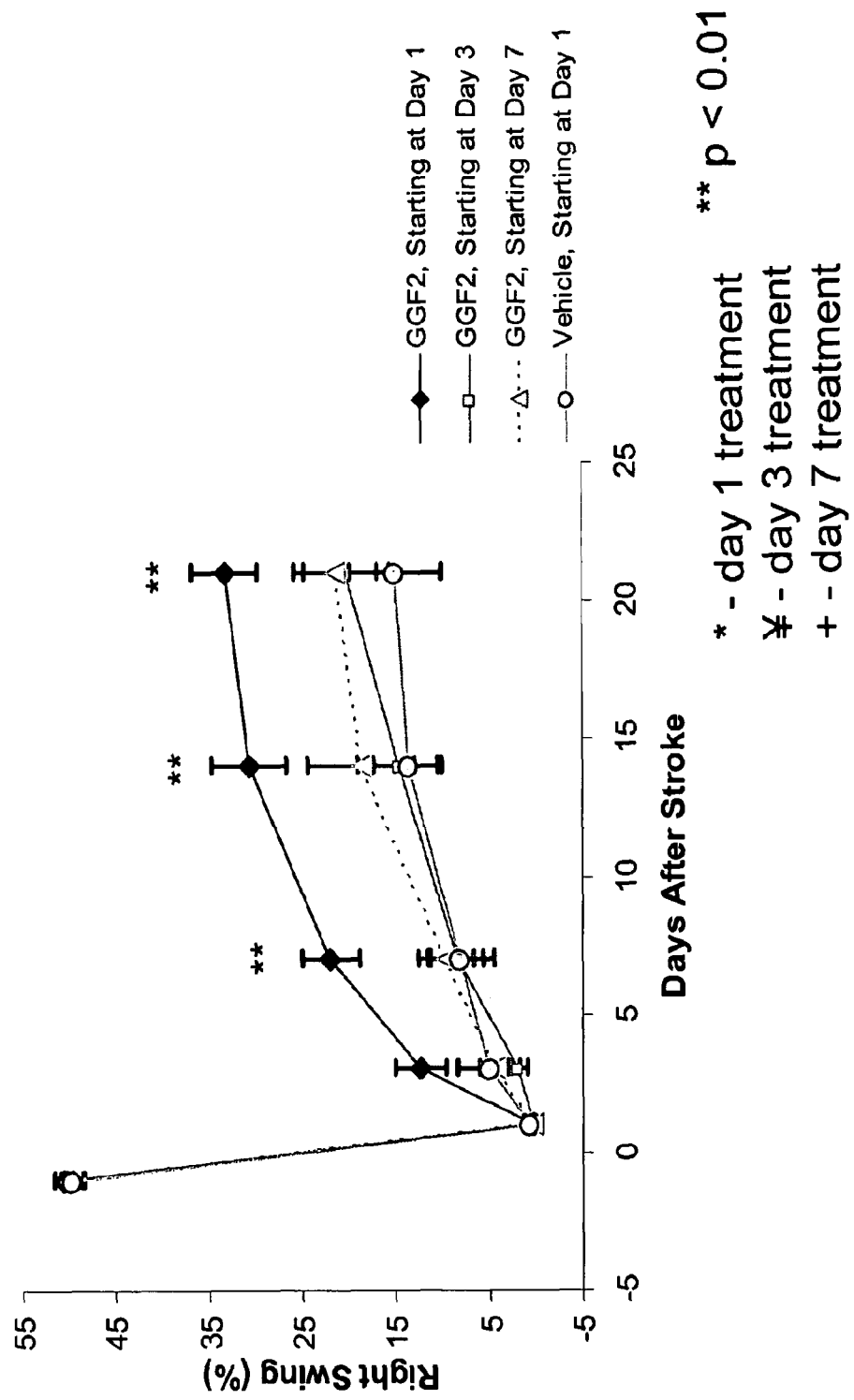
FIG. 5C shows body swing behavioral scores following permanent ligation of the middle cerebral artery. Rats were treated with GGF2 starting 1, 3 or 7 days after the ligation. GGF2 was delivered at 0.1 mg/kg, IV daily for 10 days. Body swing scores were significantly better than vehicle when treatment was initiated 1 day after ligation, and were improved compared to vehicle with treatment initiated 3 or 7 days post ligation. (*, ¥, + indicate significantly different from vehicle for the day 1, 3 and 7 treatment groups, respectively by repeated measures ANOVA and post-hoc Tukey).

Body swing: Recovery in the Day 1 GGF2 treatment group was significantly better than the vehicle group (p<0.001). There was a trend toward recovery in the Day 3 GGF2 group and Day 7 GGF2 group, compared to the vehicle group FIG. 5C.

There were no significant differences in body weights between the groups.

Infarct Volume: There were no significant differences among all groups as shown in Table 4.

TABLE 4

| Group | % Infarct volume |
| --- | --- |
| Day 1 Vehicle | 32.89 ± 2.63 |
| GGF2 Day 1 | 27.62 ± 2.48 |
| GGF2 Day 3 | 33.31 ± 3.84 |
| GGF2 Day 7 | 27.30 ± 2.87 |

Summary:

By the Day 21 study endpoint it was found that treatment initiated on Day 1, Day 3 or Day 7 post MCAO resulted in significant improvements in forelimb function compared to vehicle treated animals. Treatment initiated on Day 1, Day 3 or Day 7 post MCAO resulted in significant improvements in hindlimb function compared to vehicle treatment during specific behavioral testing points that correlated with treatment time, indicating that continued treatment may prove beneficial Functional recovery with interventions given at this later time points post injury eliminates the possibility that the effect is due to acute neuroprotection. Indeed, this data coupled with the lack of a significant change in infarct volume demonstrates that the improvements are due to the promotion of neurorecovery with GGF2 treatment. This shows that a long temporal window exists (post-acute and post-semi acute) during which time GGF2 may be administered as an effective therapeutic for the chronic phase of stroke It is, noteworthy that the significant (under ANOVA statistics) improvements observed following GGF2 administration at 3 and 7 days post-MCAO represent a dramatic expansion in the therapeutic window offered by previously available strategies for treatment of acute phase stroke. For the first time in the art, the data presented herein demonstrated that GGF2 administration is efficacious even during the chronic phase of stroke. The data presented herein further suggest that GGF2 contributes to neurorecovery following neuroinjury.

Example 4

Treatment of Ischemic Stroke

A patient presents to a medical facility with signs and symptoms of an ischemic stroke. The patient is revascularized with tPA or other therapy to restore blood flow. Although blood flow has been restored, some level of brain injury has occurred. Three days after the injury the patient is assessed neurologically and shown to have measurable sensory and/or motor deficits. Beginning on day four, after day two and after day 3, this patient would is treated with neuregulin at a dose between 0.01 and 1.0 mg/kg per dose, intravenously for 10 days to 3 months. The patient successfully regains sensory and motor function without the concomitant use of Occupational or Physical Therapy. This recovery is better than would have been clinically predicted without neuregulin therapy. This recovery is better than would have been clinically predicted without use of Occupational or Physical Therapy.

Example 5

Treatment of Stroke And Resulting Paralysis of the Right Hand

A patient presents to the Emergency Department with paralysis of the right hand. Following evaluation and imaging it is determined that the patient has suffered an ischemic stroke. The patient receives tPA according to approved methods, and blood flow is restored through the thrombosis. However, a week after tPA treatment, the patient has residual paralysis of the right hand as measured by standard neurological measures of hand motor activity. This patient is treated with neuregulin (0.01 to 1.0 mg/kg, IV) once per week for 4 weeks. Improvement in hand function is measured periodically by a neurologist or other physician with standard neurological testing including dynamometer and other strength testing. The patient successfully regains sensory and motor function in their right hand without the concomitant use of Occupational or Physical Therapy. This recovery is better than would have been clinically predicted without neuregulin therapy. This recovery is better than would have been clinically predicted without use of Occupational or Physical Therapy Example 6

Treatment of Ischemic Stroke

A patient presents to a medical facility with signs and symptoms of an ischemic stroke. They are found to have paralysis of their left side. The patient does not arrive in time for revascularization therapy with. Upon clinical evaluation it is found that some brain injury has occurred. Three days after the injury the patient is assessed neurologically and shown to have measurable sensory and motor deficits. This patient is treated with neuregulin at a dose between 0.01 and 1.0 mg/kg per dose, intravenously each day for four weeks; thereafter they receive weekly doses for six months. They also receive physical therapy. Improvement is noticed as early as the second week of treatment; recovery continues throughout the period of neuregulin therapy. The patient successfully regains sensory and motor function of their left side. This recovery is seen as excellent; and is much better than would have been clinically predicted without with the use of Physical Therapy alone.

Example 7

Treatment of Ischemic Stroke

A patient presents to the Emergency Department with paralysis of the left hand. The patient reports that the problem with their hand began "over a week ago". Following evaluation and imaging it is determined that the patient has suffered an ischemic stroke. The patient does not receive tPA. Upon neurological exam it is found that The patient has residual paralysis of the left hand as measured by standard neurological measures of hand motor activity; the patient has a sensory deficit as well. The patient refuses to participate in physical or occupational therapy. This patient treated with neuregulin (0.01 to 1.0 mg/kg, IV) once per week for 12 weeks. Improvement in hand function is measured periodically by a neurologist or other physician with the standard neurological testing including dynamometer and other strength testing. Improvement is noticed as early as the second week of treatment; recovery continues throughout the period of neuregulin therapy. The patient successfully regains sensory and motor function in their left hand without the concomitant use of Occupational or Physical Therapy. This recovery is better than would have been clinically predicted without neuregulin therapy. This recovery is better than would have been clinically predicted without use of Occupational or Physical Therapy.

Example 8

Traumatic Brain Injury

A patient presents to a medical facility following a traumatic event with signs and symptoms of a head injury and resultant brain injury. Some level of brain injury has occurred as assessed by imaging and neurological testing including Glasgow Coma Scale and more detailed neurocognitive testing. Five days after the injury, the patient is assessed neurologically and shown to have measurable sensory and motor deficits. This patient is treated with neuregulin at a dose between 0.01 and 1.0 mg/kg per dose, intravenously for 3 months. Initially the patient is not willing to participate in physical therapy. Improvement in brain function is noticed as early as the first week of treatment; recovery continues throughout the period of neuregulin therapy. This recovery is better than would have been clinically predicted without neuregulin therapy. Beginning at three months the patient begins to receive neuregulin once per week, and they also begin to receive physical therapy. The concomitant therapies continue for up until one year from the day of original injury. On the anniversary of the patient's injury their recover is extraordinary. Clinically is it far better than would have been anticipated in the absence of any therapy and is also better than would have been expected from the use of physical therapy.

Example 9

Treatment of Cerebral Hemorrhage

A patient presents to a medical facility with signs and symptoms consistent with an ischemic stroke or cerebral hemorrhage. The patient is stabilized. Upon neurological assessment it is found that some level of brain injury has occurred. One week after the injury the patient is again assessed neurologically and shown to have measurable sensory and/or motor deficits. This patient is treated with neuregulin at a dose between 0.01 and 1.0 mg/kg daily, intravenously for 10 days, followed by administration of this dose weekly for 2 months, at which point all treatment is discontinued. Improvement in brain function is noticed as early as the first week of treatment; recovery continues throughout the period of neuregulin therapy. Upon cessation of neuregulin therapy the patients recover is deemed clinically excellent. The patient returns for evaluation six months and then 12 months from the date of the initial injury; at each assessment the patient's recovery is deemed clinically excellent.

Example 10

NRG Treatment of Injury Including Treatment in Semi-Acute and Chronic Periods For a comprehensive trial, inclusion criteria include: adults, male and female, with clinical evidence of neuronjury.
Indications Explored:
Ischemic stroke with thrombolytics,
Ischemic stroke without thrombolytics,
Hemorrhagic stroke,
Closed head traumatic brain injury,
Penetrating traumatic brain injury
Dose Ranges Explored:
0.001 mg/kg to 10.0 mg/kg per dose
Dose Frequencies Explored:
daily
on alternate days
every fourth day
once per week
once every other week
once per month
Mixed Periodicity Regimens:
daily for one or two weeks and then weekly, biweekly, or monthly for the remainder of the study
on alternate days for one or two weeks and then weekly, biweekly or monthly thereafter
Initiation of Treatment Explored:
As soon as possible after injury
Within 6, 12, 24 and 48 hours after injury
After 72 hours following injury
7, 14, 30, 60, 90, 120 days following injury
Treatment Duration Explored:
treatment for 1, 2, 4, 10, 30 weeks.
treatment for 1, 2, 3, 4, 5, 6, 7, 8, 9, 10, 11, 12 months
Function Explored:
hand motor function,
face motor function,
speech
cognitive function
survival
time to return to work
Recovery is measured by standard neurological measures.
Adverse Events are mild and well-tolerated.
Results: Patients treated with neuregulin show statistically greater improvement in mental, sensory or muscle function as measured by methodologies known in the art, as compared to those patients treated with placebo.
In alternative embodiments combinations less than all of the above parameters are explored.

Example 11

NRG Treatment of Ischemic Stroke with Unilateral Hand Weakness and/or Paralysis (without Thrombolysis)

Inclusion criteria include: adults, male and female, evidence of stroke based on loss of consciousness, disorientation, speech difficulty, facial or limb paralysis. Ischemic stroke confirmed with radiographic imaging.
Patients are selected for those with unilateral hand weakness and/or paralysis that are not candidates for tPA (or other thrombolytic) or who did not previously receive tPA for any reason. Consents are obtained from the patients and/or someone with authority to sign for the patients.
Patients are enrolled and randomized to received neuregulin or placebo starting as soon as they present to a medical facility including hospital or physician's office, diagnosis, imaging is obtained.
For this trial, treatment is initiated between 1 hour and 7 days after injury. Treatment is continued for 3 months with dosing on alternate days for 1 week and then weekly for the remainder of the treatment period. Patients are dosed with 0.0001 to 1.0 mg per kg, IV, IM or SC.
Recovery is measured by standard neurological measures of hand motor activity every other week for the duration of the study.
Adverse Events are mild and well-tolerated.
Results: Patients treated with neuregulin show statistically greater improvement in hand function as measured by methodologies known in the art, as compared to those patients treated with placebo.

Example 12

NRG Treatment of Unilateral Facial Paralysis without Thrombolytics

Patients are selected for those with unilateral facial paralysis who did not or cannot receive thrombolytics. Function is assessed by methodologies known in the art, on alternate weeks during the 3 month dosing period. Consents are obtained from the patients and/or someone with authority to sign for the patients.
Patients are enrolled and randomized to received neuregulin or placebo. Treatment is initiated between 1 hour and 7 days after injury. Treatment is continued for 3 months with dosing on alternate days for 1 week and then weekly for the remainder of the treatment period. Patients are dosed with 0.0001 to 1.0 mg per kg, IV, IM or SC.
Adverse Events are mild and well-tolerated.
Results: Patients treated with neuregulin show statistically greater improvement in facial movement than those patients treated with placebo.

Example 13

NRG Treatment of Aphasia or Dysarthria without Thrombolytics

Patients are selected for those with aphasia or dysarthria who did not or cannot receive thrombolytics. Function is assessed by methodologies known in the art. on alternate weeks during the 3 month dosing period. Consents are obtained from the patients and/or someone with authority to sign for the patients.
Patients are enrolled and randomized to received neuregulin or placebo. Treatment is initiated between 1 hour and 7 days after injury. Treatment is continued for 3 months with dosing on alternate days for 1 week and then weekly for the remainder of the treatment period. Patients are dosed with 0.0001 to 1.0 mg per kg, IV, IM or SC.
Adverse Events are mild and well-tolerated.
Results: Patients treated with neuregulin show statistically greater improvement in speech capability than those patients treated with placebo.

Example 14

NRG Treatment of Ischemic Stroke (with Thrombolysis)

Inclusion criteria include: adults, male and female, evidence of stroke based on loss of consciousness, disorientation, speech difficulty, facial or limb paralysis. Ischemic stroke is confirmed with radiographic imaging.

Patients are selected for those with unilateral hand weakness and/or paralysis that and are successfully treated with tPA or other thrombolytic. Consents are obtained from the patients and/or someone with authority to sign for the patients Patients are enrolled and randomized to received neuregulin or placebo starting as soon as they present to a medical facility, diagnosis, and imaging is completed.

Treatment is initiated between 1 hour and 7 days after injury. Treatment is continued for 3 months with dosing on alternate days for 1 week and then weekly for the remainder of the treatment period. Patients are dosed with 0.0001 to 1.0 mg per kg, IV, IM or SC.

Recovery is measured by standard neurological measures of hand motor activity every other week for the duration of the study.

Adverse Events are generally mild and well tolerated.

Results: Patients treated with neuregulin show statistically greater improvement in hand function as measured by methodologies known in the art as compared to those patients treated with placebo.

Example 15

NRG Treatment of Patients with Unilateral Facial Paralysis (with Thrombolytics)

Inclusion criteria include: adults, male and female, evidence of stroke based on loss of consciousness, disorientation, speech difficulty, facial or limb paralysis. Ischemic stroke is confirmed with radiographic imaging. Patients are selected for those with aphasia or dysarthria and did receive thrombolytics.

Treatment is initiated between 1 hour and 7 days after injury. Treatment is continued for 3 months with dosing on alternate days for 1 week and then weekly for the remainder of the treatment period. Patients are dosed with 0.0001 to 1.0 mg per kg, IV, IM or SC.

Function is assessed by methodologies known in the art, on alternate weeks during the 3 month dosing period.

Adverse Events are mild and well-tolerated.

Results: Patients treated with neuregulin show statistically greater improvement in speech capability than those patients treated with placebo.

Example 16

NRG Treatment of Patients with Traumatic Brain Injury

Inclusion criteria include: adults, male and female, evidence of traumatic brain injury with loss of consciousness, disorientation, speech difficulty, facial or limb paralysis with evidence or history of trauma. Patients with evidence of penetrating injury are excluded. Consents are obtained from the patients and/or someone with authority to sign for the patients.

Patients are enrolled and randomized to received neuregulin or placebo starting as soon as they present to a medical facility including hospital or physician's office, diagnosis, imaging and consent is obtained.

For this trial treatment is initiated between 1 hour and 7 days after injury. Treatment is continued for 3 months with dosing on alternate days for 1 week and then weekly for the remainder of the treatment period. Patients are dosed with 0.0001 to 1.0 mg per kg, IV, IM or SC.

Functional recovery is assessed by methodologies known in the art.

Adverse Events are mild and well-tolerated.

Results: Patients treated with neuregulin show statistically greater improvement than those patients treated with placebo.

Example 17

NRG Treatment of Patients with Penetrating Brain Injury

Inclusion criteria include: adults, male and female, evidence of traumatic brain injury with loss of consciousness, disorientation, speech difficulty, facial or limb paralysis with evidence or history of trauma. Consents are obtained from the patients and/or someone with authority to sign for the patients.

Patients are stabilized surgically or through other measures. Diagnosis and imaging are obtained.

Patients are enrolled and randomized to received neuregulin or placebo starting as soon as they present to a medical facility including hospital or physicians office.

Treatment is initiated between 1 hour and 7 days after injury. Treatment is continued for 3 months with dosing on alternate days for 1 week and then weekly for the remainder of the treatment period. Patients are dosed with 0.0001 to 1.0 mg per kg, IV, IM or SC.

Functional recovery is assessed by methodologies known in the art.

Adverse Events are mild and well-tolerated.

Results: Patients treated with neuregulin show statistically greater improvement in speech capability than those patients treated with placebo.

Example 18

NRG Treatment of Patients with Hemorrhagic Stroke

Inclusion criteria include: adults, male and female, evidence of stroke based on loss of consciousness, disorientation, speech difficulty, facial or limb paralysis. Hemorrhagic stroke confirmed with radiographic imaging. Consents are obtained from the patients and/or someone with authority to sign for the patients.

Patients are selected for those with unilateral hand weakness

Patients are enrolled and randomized to received neuregulin or placebo starting as soon as they present to a medical facility including hospital or physician's office, diagnosis, imaging and consent is obtained.

Treatment is initiated between 1 hour and 7 days after injury. Treatment is continued for 3 months with dosing on alternate days for 1 week and then weekly for the remainder of the treatment period. Patients are dosed with 0.0001 to 1.0 mg per kg, IV, IM or SC.

Recovery is measured by standard neurological measures of hand motor activity every other week for the duration of the study.

Adverse Events are mild and well-tolerated.

Results: Patients treated with neuregulin show statistically greater improvement in hand function as measured by methodologies known in the art as compared to those patients treated with placebo.

Example 19

Kits

Kits comprise an exemplary embodiment of the invention. The kit can comprise an outer receptacle or container configured to receive one or more inner receptacles/containers, utensils and/or instructions. The utensil can comprise item(s) to administer the drug, such as a patch, inhalation apparatus, syringe or needle. A composition of the invention can be comprised within a receptacle of the invention. A receptacle of the invention can contain sufficient quantity of a composition of the invention to be useful for multiple doses, or may be in unit or single dose form. Kits of the invention generally comprise instructions for administration in accordance with the present invention. Any mode of administration set forth or supported herein can constitute some portion of the instructions. In one embodiment the instructions indicate that the composition of the invention is to be taken one or more than one times during the semi-acute post-injury period. In one embodiment the instructions indicate that the composition of the invention is to be taken one or more than one times during the chronic post-injury period. The instructions may be affixed to any container/receptacle of the invention. Alternatively, the instructions can be printed on or embossed in or formed as a component of a receptacle of the invention.

Several publications and patent documents are referenced in this application in order to more fully describe the state of the art to which this invention pertains. All publications and patent applications mentioned in this specification are herein incorporated by reference to the same extent as if each independent publication or patent application was specifically and individually indicated to be incorporated by reference.

What is claimed is:

1. A method for treating a neuroinjury resulting from a stroke in a mammal comprising administering a polypeptide comprising an epidermal growth factor like (EGF-like) domain of Glial Growth Factor 2 (GGF2), wherein the EGF-like domain comprises the amino acid sequence of SEQ ID NO: 18, to the mammal following said neuroinjury in said mammal, wherein the administering step is initiated at least one day after said neuroinjury.

2. The method of claim 1, wherein said administering step begins at least three days after the neuroinjury.

3. The method of claim 1, wherein said administering step begins at least seven days after the neuroinjury.

4. The method of claim 1, wherein said mammal is a human.

5. The method of claim 1, wherein the stroke is an ischemic stroke or a hemorrhagic stroke.

6. The method of claim 1, wherein the GGF2 polypeptide is administered at a dose of 0.01-1 mg/kg bodyweight.

7. The method of claim 1, wherein said administering step begins at least two days after the neuroinjury.

8. A method for treating a neuroinjury resulting from a stroke in a mammal comprising administering a polypeptide comprising an epidermal growth factor like (EGF-like) domain of Glial Growth Factor 2 (GGF2), wherein the EGF-like domain comprises the amino acid sequence of SEQ ID NO: 18, to the mammal following said neuroinjury in said mammal, wherein the administering step is initiated within six hours after said neuroinjury and wherein the administering step is continued into a time period more than six hours post injury.

9. The method of claim 8, wherein the administering step is continued into a time period more than 48 hours post injury.

10. The method of claim 8, wherein the administering step is continued into a time period more than 72 hours post injury.

11. The method of claim 8, wherein said mammal is a human.

12. The method of claim 8, wherein the stroke is an ischemic stroke or a hemorrhagic stroke.

13. The method of claim 8, wherein the polypeptide is administered at a dose of 0.01-1 mg/kg bodyweight.

14. A method for treating an ischemic central nervous system neuroinjury in a mammal comprising administering a polypeptide comprising an epidermal growth factor like (EGF-like) domain of Glial Growth Factor 2 (GGF2), wherein the EGF-like domain comprises the amino acid sequence of SEQ ID NO: 18, to the mammal following neuroinjury in said mammal, wherein the administering step is initiated after the mammal has achieved a complete post-injury ischemic lesion cell death volume.

15. The method of claim 14, wherein the neuroinjury results from a stroke.

16. The method of claim 14, wherein the polypeptide is administered at a dose of 0.01-1 mg/kg bodyweight.

* * * * *

```
                       SEQUENCE LISTING

<160> NUMBER OF SEQ ID NOS: 53

<210> SEQ ID NO 1
<211> LENGTH: 198
<212> TYPE: DNA
<213> ORGANISM: Homo sapiens

<400> SEQUENCE: 1
catatgagcc atcttgtaaa atgtgcggag aaggagaaaa ctttctgtgt gaatggaggg     60
gagtgcttca tggtgaaaga cctttcaaac ccctcgagat acttgtgcaa gtgcccaaat    120
gagtttactg gtgatcgctg ccaaaactac gtaatggcca gcttctacaa ggcggaggag    180
ctgtaccagt aaggatcc                                                 198

<210> SEQ ID NO 2
<211> LENGTH: 82
<212> TYPE: PRT
<213> ORGANISM: Homo sapiens

<400> SEQUENCE: 2

Met Gly Ser Ser His His His His His His Ser Ser Gly Leu Val Pro
1               5                   10                  15

Arg Gly Ser His Met Ser His Leu Val Lys Cys Ala Glu Lys Glu Lys
                20                  25                  30

Thr Phe Cys Val Asn Gly Gly Glu Cys Phe Met Val Lys Asp Leu Ser
            35                  40                  45

Asn Pro Ser Arg Tyr Leu Cys Lys Cys Pro Asn Glu Phe Thr Gly Asp
        50                  55                  60

Arg Cys Gln Asn Tyr Val Met Ala Ser Phe Tyr Lys Ala Glu Glu Leu
65                  70                  75                  80

Tyr Gln

<210> SEQ ID NO 3
<211> LENGTH: 236
<212> TYPE: DNA
<213> ORGANISM: Artificial Sequence
<220> FEATURE:
<223> OTHER INFORMATION: Recombinant sequence

<400> SEQUENCE: 3
cgataactag cagcatttcc tccaacgagg atcccgcagg taagaagcta caccggccag     60
tggccggggc ccgataacta gcagcatttc ctccaacgag gatcccgcag gtaagaagct    120
```
acaccggcca gtggccgggg ccgtggagcc gggggcatcc ggtgcctgag acagaggtgc    180
tcaaggcagt ctccaccttt tgtctcccct ctgcagagag ccacattctg gaagtt       236

<210> SEQ ID NO 4
<211> LENGTH: 1269
<212> TYPE: DNA
<213> ORGANISM: Homo sapiens

<400> SEQUENCE: 4
atgagatggc gacgcgcccc gcgccgctcc gggcgtcccg gccccgggc ccagcgcccc     60 ggctccgccg cccgctcgtc gccgccgctg ccgctgctgc cactactgct gctgctgggg   120
accgcggccc tggcgccggg ggcggcggcc ggcaacgagg cggctcccgc gggggcctcg   180
gtgtgctact cgtccccgcc cagcgtggga tcggtgcagg agctagctca gcgcgccgcg   240
gtggtgatcg agggaaaggt gcacccgcag cggcggcagc aggggggcact cgacaggaag   300 gcggcggcgg cggcgggcga ggcagggggcg tggggcggcg atcgcgagcc gccagccgcg   360
ggcccacggg cgctggggcc gcccgccgag gagccgctgc tcgccgccaa cgggaccgtg   420
ccctcttggc ccaccgcccc ggtgcccagc gccggcgagc ccggggagga ggcgccctat   480
ctggtgaagg tgcaccaggt gtgggcggtg aaagccgggg gcttgaagaa ggactcgctg   540
ctcaccgtgc gcctggggac ctggggccac ccgccttcc cctcctgcgg gaggctcaag    600
gaggacagca ggtacatctt cttcatggag cccgacgcca acagcaccag ccgcgcgccg   660
gccgccttcc gagcctcttt ccccctctg gagacgggcc ggaacctcaa gaaggaggtc    720
agccgggtgc tgtgcaagcg gtgcgccttg cctccccaat tgaaagagat gaaaagccag   780
gaatcggctg caggttccaa actagtcctt cggtgtgaaa ccagttctga atactcctct   840
ctcagattca agtggttcaa gaatgggaat gaattgaatc gaaaaaacaa accacaaaat   900
atcaagatac aaaaaaagcc agggaagtca gaacttcgca ttaacaaagc atcactggct   960
gattctggag agtatatgtg caaagtgatc agcaaattag gaaatgacag tgcctctgcc  1020
aatatcacca tcgtggaatc aaacgctaca tctacatcca ccactgggac aagccatctt  1080
gtaaaatgtg cggagaagga gaaaactttc tgtgtgaatg gggggagtg cttcatggtg   1140 aaagaccttt caaacccctc gagatacttg tgcaagtgcc caatgagtt tactggtgat  1200 cgctgccaaa actacgtaat ggccagcttc tacagtacgt ccactcccttt tctgtctctg  1260 cctgaatag                                                         1269

<210> SEQ ID NO 5
<211> LENGTH: 422
<212> TYPE: PRT
<213> ORGANISM: Homo sapiens

<400> SEQUENCE: 5

Met Arg Trp Arg Arg Ala Pro Arg Arg Ser Gly Arg Pro Gly Pro Arg
1               5                   10                  15

Ala Gln Arg Pro Gly Ser Ala Ala Arg Ser Ser Pro Pro Leu Pro Leu
                20                  25                  30

Leu Pro Leu Leu Leu Leu Leu Gly Thr Ala Ala Leu Ala Pro Gly Ala
            35                  40                  45

Ala Ala Gly Asn Glu Ala Ala Pro Ala Gly Ala Ser Val Cys Tyr Ser
        50                  55                  60

Ser Pro Pro Ser Val Gly Ser Val Gln Glu Leu Ala Gln Arg Ala Ala
65                  70                  75                  80

```
Val Val Ile Glu Gly Lys Val His Pro Gln Arg Gln Gln Gly Ala
                85                  90                  95

Leu Asp Arg Lys Ala Ala Ala Ala Gly Glu Ala Gly Ala Trp Gly
            100                 105                 110

Gly Asp Arg Glu Pro Pro Ala Ala Gly Pro Arg Ala Leu Gly Pro Pro
        115                 120                 125

Ala Glu Glu Pro Leu Leu Ala Ala Asn Gly Thr Val Pro Ser Trp Pro
    130                 135                 140

Thr Ala Pro Val Pro Ser Ala Gly Glu Pro Gly Glu Glu Ala Pro Tyr
145                 150                 155                 160

Leu Val Lys Val His Gln Val Trp Ala Val Lys Ala Gly Gly Leu Lys
                165                 170                 175

Lys Asp Ser Leu Leu Thr Val Arg Leu Gly Thr Trp Gly His Pro Ala
            180                 185                 190

Phe Pro Ser Cys Gly Arg Leu Lys Glu Asp Ser Arg Tyr Ile Phe Phe
        195                 200                 205

Met Glu Pro Asp Ala Asn Ser Thr Ser Arg Ala Pro Ala Ala Phe Arg
    210                 215                 220

Ala Ser Phe Pro Pro Leu Glu Thr Gly Arg Asn Leu Lys Lys Glu Val
225                 230                 235                 240

Ser Arg Val Leu Cys Lys Arg Cys Ala Leu Pro Pro Gln Leu Lys Glu
                245                 250                 255

Met Lys Ser Gln Glu Ser Ala Ala Gly Ser Lys Leu Val Leu Arg Cys
            260                 265                 270

Glu Thr Ser Ser Glu Tyr Ser Ser Leu Arg Phe Lys Trp Phe Lys Asn
        275                 280                 285

Gly Asn Glu Leu Asn Arg Lys Asn Lys Pro Gln Asn Ile Lys Ile Gln
    290                 295                 300

Lys Lys Pro Gly Lys Ser Glu Leu Arg Ile Asn Lys Ala Ser Leu Ala
305                 310                 315                 320

Asp Ser Gly Glu Tyr Met Cys Lys Val Ile Ser Lys Leu Gly Asn Asp
                325                 330                 335

Ser Ala Ser Ala Asn Ile Thr Ile Val Glu Ser Asn Ala Thr Ser Thr
            340                 345                 350

Ser Thr Thr Gly Thr Ser His Leu Val Lys Cys Ala Glu Lys Glu Lys
        355                 360                 365

Thr Phe Cys Val Asn Gly Gly Glu Cys Phe Met Val Lys Asp Leu Ser
    370                 375                 380

Asn Pro Ser Arg Tyr Leu Cys Lys Cys Pro Asn Glu Phe Thr Gly Asp
385                 390                 395                 400

Arg Cys Gln Asn Tyr Val Met Ala Ser Phe Tyr Ser Thr Ser Thr Pro
                405                 410                 415

Phe Leu Ser Leu Pro Glu
            420

<210> SEQ ID NO 6
<211> LENGTH: 2003
<212> TYPE: DNA
<213> ORGANISM: Homo sapiens
<220> FEATURE:
<221> NAME/KEY: misc_feature
<222> LOCATION: (31)..(32)
<223> OTHER INFORMATION: n is a, c, g, or t
```

<400> SEQUENCE: 6

```
ggaattcctt tttttttttt tttttttctt nntttttttt tgcccttata cctcttcgcc      60
tttctgtggt tccatccact tcttcccct cctcctccca taaacaactc tcctacccct     120
gcaccccaa taaataaata aaaggaggag ggcaaggggg gaggaggagg agtggtgctg     180
cgagggaag gaaaagggag gcagcgcgag aagagccggg cagagtccga accgacagcc     240
agaagcccgc acgcacctcg caccatgaga tggcgacgcg ccccgcgccg ctccgggcgt     300
cccggccccc gggcccagcg ccccggctcc gccgcccgct cgtcgccgcc gctgccgctg     360
ctgccactac tgctgctgct ggggaccgcg gccctggcgc cggggcggc ggccggcaac     420
gaggcggctc ccgcggggc ctcggtgtgc tactcgtccc cgcccagcgt gggatcggtg     480
caggagctag ctcagcgcgc cgcggtggtg atcgagggaa aggtgcaccc gcagcggcgg     540
cagcagggg cactcgacag gaaggcggcg gcggcggcgg gcgaggcagg ggcgtggggc     600
ggcgatcgcg agccgccagc cgcgggccca cgggcgctgg ggccgcccgc cgaggagccg     660
ctgctcgccg ccaacgggac cgtgccctct tggcccaccg ccccggtgcc cagcgccggc     720
gagcccgggg aggaggcgcc ctatctggtg aaggtgcacc aggtgtgggc ggtgaaagcc     780
ggggggcttga agaaggactc gctgctcacc gtgcgcctgg ggacctgggg ccaccccgcc     840
ttcccctcct gcgggaggct caaggaggac agcaggtaca tcttcttcat ggagcccgac     900
gccaacagca ccagccgcgc gccggccgcc ttccgagcct cttcccccc tctggagacg     960
ggccggaacc tcaagaagga ggtcagccgg gtgctgtgca agcggtgcgc cttgcctccc    1020
caattgaaag agatgaaaag ccaggaatcg gctgcaggtt ccaaactagt ccttcggtgt    1080
gaaaccagtt ctgaatactc ctctctcaga ttcaagtggt tcaagaatgg gaatgaattg    1140
aatcgaaaaa acaaaccaca aaatatcaag atacaaaaaa agccagggaa gtcagaactt    1200
cgcattaaca aagcatcact ggctgattct ggagagtata tgtgcaaagt gatcagcaaa    1260
ttaggaaatg acagtgcctc tgccaatatc accatcgtgg aatcaaacgc tacatctaca    1320
tccaccactg ggacaagcca tcttgtaaaa tgtgcggaga aggagaaaac tttctgtgtg    1380
aatggagggg agtgcttcat ggtgaaagac cttcaaacc cctcgagata cttgtgcaag    1440
tgcccaaatg agtttactgg tgatcgctgc caaaactacg taatggccag cttctacagt    1500
acgtccactc cctttctgtc tctgcctgaa taggagcatg ctcagttggt gctgctttct    1560
tgttgctgca tctcccctca gattccacct agagctagat gtgtcttacc agatctaata    1620
ttgactgcct ctgcctgtcg catgagaaca ttaacaaaag caattgtatt acttcctctg    1680
ttcgcgacta gttggctctg agatactaat aggtgtgtga ggctccggat gtttctggaa    1740
ttgatattga atgatgtgat acaaattgat agtcaatatc aagcagtgaa atatgataat    1800
aaaggcattt caaagtctca cttttattga taaaataaaa atcattctac tgaacagtcc    1860
atcttctta tacaatgacc acatcctgaa aagggtgttg ctaagctgta accgatatgc    1920
acttgaaatg atggtaagtt aattttgatt cagaatgtgt tatttgtcac aaataaacat    1980
aataaaagga aaaaaaaaaa aaa                                             2003
```

<210> SEQ ID NO 7
<211> LENGTH: 422
<212> TYPE: PRT
<213> ORGANISM: Homo sapiens

<400> SEQUENCE: 7

```
Met Arg Trp Arg Arg Ala Pro Arg Arg Ser Gly Arg Pro Gly Pro Arg
1               5                   10                  15

Ala Gln Arg Pro Gly Ser Ala Ala Arg Ser Ser Pro Pro Leu Pro Leu
                20                  25                  30

Leu Pro Leu Leu Leu Leu Leu Gly Thr Ala Ala Leu Ala Pro Gly Ala
            35                  40                  45

Ala Ala Gly Asn Glu Ala Ala Pro Ala Gly Ala Ser Val Cys Tyr Ser
            50                  55                  60

Ser Pro Pro Ser Val Gly Ser Val Gln Glu Leu Ala Gln Arg Ala Ala
65                  70                  75                  80

Val Val Ile Glu Gly Lys Val His Pro Gln Arg Arg Gln Gly Ala
                85                  90                  95

Leu Asp Arg Lys Ala Ala Ala Ala Gly Glu Ala Gly Ala Trp Gly
                100                 105                 110

Gly Asp Arg Glu Pro Pro Ala Ala Gly Pro Arg Ala Leu Gly Pro Pro
                115                 120                 125

Ala Glu Glu Pro Leu Leu Ala Ala Asn Gly Thr Val Pro Ser Trp Pro
            130                 135                 140

Thr Ala Pro Val Pro Ser Ala Gly Glu Pro Gly Glu Glu Ala Pro Tyr
145                 150                 155                 160

Leu Val Lys Val His Gln Val Trp Ala Val Lys Ala Gly Gly Leu Lys
                165                 170                 175

Lys Asp Ser Leu Leu Thr Val Arg Leu Gly Thr Trp Gly His Pro Ala
                180                 185                 190

Phe Pro Ser Cys Gly Arg Leu Lys Glu Asp Ser Arg Tyr Ile Phe Phe
                195                 200                 205

Met Glu Pro Asp Ala Asn Ser Thr Ser Arg Ala Pro Ala Ala Phe Arg
            210                 215                 220

Ala Ser Phe Pro Pro Leu Glu Thr Gly Arg Asn Leu Lys Lys Glu Val
225                 230                 235                 240

Ser Arg Val Leu Cys Lys Arg Cys Ala Leu Pro Pro Gln Leu Lys Glu
                245                 250                 255

Met Lys Ser Gln Glu Ser Ala Ala Gly Ser Lys Leu Val Leu Arg Cys
                260                 265                 270

Glu Thr Ser Ser Glu Tyr Ser Ser Leu Arg Phe Lys Trp Phe Lys Asn
            275                 280                 285

Gly Asn Glu Leu Asn Arg Lys Asn Lys Pro Gln Asn Ile Lys Ile Gln
290                 295                 300

Lys Lys Pro Gly Lys Ser Glu Leu Arg Ile Asn Lys Ala Ser Leu Ala
305                 310                 315                 320

Asp Ser Gly Glu Tyr Met Cys Lys Val Ile Ser Lys Leu Gly Asn Asp
                325                 330                 335

Ser Ala Ser Ala Asn Ile Thr Ile Val Glu Ser Asn Ala Thr Ser Thr
                340                 345                 350

Ser Thr Thr Gly Thr Ser His Leu Val Lys Cys Ala Glu Lys Glu Lys
                355                 360                 365

Thr Phe Cys Val Asn Gly Gly Glu Cys Phe Met Val Lys Asp Leu Ser
            370                 375                 380

Asn Pro Ser Arg Tyr Leu Cys Lys Cys Pro Asn Glu Phe Thr Gly Asp
385                 390                 395                 400
```

```
Arg Cys Gln Asn Tyr Val Met Ala Ser Phe Tyr Ser Thr Ser Thr Pro
                405                 410                 415

Phe Leu Ser Leu Pro Glu
            420

<210> SEQ ID NO 8
<211> LENGTH: 11
<212> TYPE: PRT
<213> ORGANISM: Homo sapiens

<400> SEQUENCE: 8

Val Cys Leu Leu Thr Val Ala Ala Leu Pro Pro
1               5                   10

<210> SEQ ID NO 9
<211> LENGTH: 15
<212> TYPE: PRT
<213> ORGANISM: Homo sapiens

<400> SEQUENCE: 9

Ala Ser Pro Val Ser Val Gly Ser Val Gln Glu Leu Val Gln Arg
1               5                   10                  15

<210> SEQ ID NO 10
<211> LENGTH: 8
<212> TYPE: PRT
<213> ORGANISM: Homo sapiens

<400> SEQUENCE: 10

Trp Phe Val Val Ile Glu Gly Lys
1               5

<210> SEQ ID NO 11
<211> LENGTH: 9
<212> TYPE: PRT
<213> ORGANISM: Homo sapiens

<400> SEQUENCE: 11

Lys Val His Glu Val Trp Ala Ala Lys
1               5

<210> SEQ ID NO 12
<211> LENGTH: 6
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Xaa can be any naturally occurring amino acid

<400> SEQUENCE: 12

Asp Leu Leu Leu Xaa Val
1               5

<210> SEQ ID NO 13
<211> LENGTH: 13
<212> TYPE: PRT
<213> ORGANISM: Homo sapiens
<220> FEATURE:
<221> NAME/KEY: misc_feature
<222> LOCATION: (12)..(12)
<223> OTHER INFORMATION: Xaa can be any naturally occurring amino acid

<400> SEQUENCE: 13

Leu Gly Ala Trp Gly Pro Pro Ala Phe Pro Val Xaa Tyr
1               5                   10
```

```
<210> SEQ ID NO 14
<211> LENGTH: 13
<212> TYPE: PRT
<213> ORGANISM: Homo sapiens
<220> FEATURE:
<221> NAME/KEY: misc_feature
<222> LOCATION: (10)..(10)
<223> OTHER INFORMATION: Xaa can be any naturally occurring amino acid

<400> SEQUENCE: 14

Tyr Ile Phe Phe Met Glu Pro Ala Ala Xaa Ser Ser Gly
1               5                   10

<210> SEQ ID NO 15
<211> LENGTH: 4
<212> TYPE: PRT
<213> ORGANISM: Homo sapiens

<400> SEQUENCE: 15

Leu Val Leu Arg
1

<210> SEQ ID NO 16
<211> LENGTH: 13
<212> TYPE: PRT
<213> ORGANISM: Homo sapiens
<220> FEATURE:
<221> NAME/KEY: misc_feature
<222> LOCATION: (12)..(12)
<223> OTHER INFORMATION: Xaa can be any naturally occurring amino acid

<400> SEQUENCE: 16

Lys Ala Ser Leu Ala Asp Ser Gly Glu Tyr Met Xaa Lys
1               5                   10

<210> SEQ ID NO 17
<211> LENGTH: 198
<212> TYPE: DNA
<213> ORGANISM: Homo sapiens

<400> SEQUENCE: 17
agccatcttg tcaagtgtgc agagaaggag aaaactttct gtgtgaatgg aggcgagtgc      60
ttcatggtga aagagctttc aaatccctca agatacttgt gcaagtgccc aaatgagttt     120
actggtgatc gctgccaaaa ctacgtaatg gccagcttct acagtacctc cactccctt     180 ctgtctctgc ctgaatag                                                   198

<210> SEQ ID NO 18
<211> LENGTH: 65
<212> TYPE: PRT
<213> ORGANISM: Homo sapiens

<400> SEQUENCE: 18

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
                20                  25                  30

Leu Cys Lys Cys Pro Asn Glu Phe Thr Gly Asp Arg Cys Gln Asn Tyr
            35                  40                  45

Val Met Ala Ser Phe Tyr Ser Thr Ser Thr Pro Phe Leu Ser Leu Pro
        50                  55                  60

Glu
65
```

<210> SEQ ID NO 19
<211> LENGTH: 192
<212> TYPE: DNA
<213> ORGANISM: Homo sapiens

<400> SEQUENCE: 19

```
agccatcttg tcaagtgtgc agagaaggag aaaactttct gtgtgaatgg aggcgagtgc      60
ttcatggtga aagacctttc aaatccctca agatacttgt gcaagtgcca acctggattc     120
actggagcga gatgtactga gaatgtgccc atgaaagtcc aaacccaaga aaaagcggag     180
gagctctact aa                                                         192
```

<210> SEQ ID NO 20
<211> LENGTH: 63
<212> TYPE: PRT
<213> ORGANISM: Homo sapiens

<400> SEQUENCE: 20

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Gln Pro Gly Phe Thr Gly Ala Arg Cys Thr Glu Asn
        35                  40                  45

Val Pro Met Lys Val Gln Thr Gln Glu Lys Ala Glu Glu Leu Tyr
    50                  55                  60

<210> SEQ ID NO 21
<211> LENGTH: 183
<212> TYPE: DNA
<213> ORGANISM: Homo sapiens

<400> SEQUENCE: 21

```
agccatcttg tcaagtgtgc agagaaggag aaaactttct gtgtgaatgg aggcgagtgc      60
ttcatggtga aagacctttc aaatccctca agatacttgt gcaagtgccc aaatgagttt     120
actggtgatc gctgccaaaa ctacgtaatg ccagcttct acaaagcgga ggagctctac     180
taa                                                                   183
```

<210> SEQ ID NO 22
<211> LENGTH: 60
<212> TYPE: PRT
<213> ORGANISM: Homo sapiens

<400> SEQUENCE: 22

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser Phe Tyr Lys Ala Glu Glu Leu Tyr
    50                  55                  60

<210> SEQ ID NO 23
<211> LENGTH: 210
<212> TYPE: DNA
<213> ORGANISM: Homo sapiens

<400> SEQUENCE: 23

```
agccatcttg tcaagtgtgc agagaaggag aaaactttct gtgtgaatgg aggcgagtgc    60
ttcatggtga aagaccttc aaatccctca agatacttgt gcaagtgccc aaatgagttt    120
actggtgatc gctgccaaaa ctacgtaatg gccagcttct acaagcatct tgggattgaa   180
tttatggaga aagcggagga gctctactaa                                    210
```

<210> SEQ ID NO 24
<211> LENGTH: 69
<212> TYPE: PRT
<213> ORGANISM: Homo sapiens

<400> SEQUENCE: 24

```
Ser His Leu Val Lys Cys Ala Glu Lys Glu Lys Thr Phe Cys Val Asn
1               5                   10                  15
Gly Gly Glu Cys Phe Met Val Lys Asp Leu Ser Asn Pro Ser Arg Tyr
            20                  25                  30
Leu Cys Lys Cys Pro Asn Glu Phe Thr Gly Asp Arg Cys Gln Asn Tyr
        35                  40                  45
Val Met Ala Ser Phe Tyr Lys His Leu Gly Ile Glu Phe Met Glu Lys
    50                  55                  60
Ala Glu Glu Leu Tyr
65
```

<210> SEQ ID NO 25
<211> LENGTH: 267
<212> TYPE: DNA
<213> ORGANISM: Homo sapiens

<400> SEQUENCE: 25

```
agccatcttg tcaagtgtgc agagaaggag aaaactttct gtgtgaatgg aggcgagtgc    60
ttcatggtga aagaccttc aaatccctca agatacttgt gcaagtgcca acctggattc   120
actggagcga gatgtactga gaatgtgccc atgaaagtcc aaacccaaga aaagtgccca   180
aatgagttta ctggtgatcg ctgccaaaac tacgtaatgg ccagcttcta cagtacgtcc   240
actccctttc tgtctctgcc tgaatag                                       267
```

<210> SEQ ID NO 26
<211> LENGTH: 88
<212> TYPE: PRT
<213> ORGANISM: Homo sapiens

<400> SEQUENCE: 26

```
Ser His Leu Val Lys Cys Ala Glu Lys Glu Lys Thr Phe Cys Val Asn
1               5                   10                  15
Gly Gly Glu Cys Phe Met Val Lys Asp Leu Ser Asn Pro Ser Arg Tyr
            20                  25                  30
Leu Cys Lys Cys Gln Pro Gly Phe Thr Gly Ala Arg Cys Thr Glu Asn
        35                  40                  45
Val Pro Met Lys Val Gln Thr Gln Glu Lys Cys Pro Asn Glu Phe Thr
    50                  55                  60
Gly Asp Arg Cys Gln Asn Tyr Val Met Ala Ser Phe Tyr Ser Thr Ser
65                  70                  75                  80
Thr Pro Phe Leu Ser Leu Pro Glu
            85
```

<210> SEQ ID NO 27
<211> LENGTH: 252
<212> TYPE: DNA
<213> ORGANISM: Homo sapiens

<400> SEQUENCE: 27

```
agccatcttg tcaagtgtgc agagaaggag aaaactttct gtgtgaatgg aggcgagtgc    60
ttcatggtga aagacctttc aaatccctca agatacttgt gcaagtgcca acctggattc   120
actggagcga gatgtactga aatgtgccc atgaaagtcc aaacccaaga aaagtgccca   180
aatgagttta ctggtgatcg ctgccaaaac tacgtaatgg ccagcttcta caaagcggag   240
gagctctact aa                                                       252
```

<210> SEQ ID NO 28
<211> LENGTH: 83
<212> TYPE: PRT
<213> ORGANISM: Homo sapiens

<400> SEQUENCE: 28

```
Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Gln Pro Gly Phe Thr Gly Ala Arg Cys Thr Glu Asn
        35                  40                  45

Val Pro Met Lys Val Gln Thr Gln Glu Lys Cys Pro Asn Glu Phe Thr
    50                  55                  60

Gly Asp Arg Cys Gln Asn Tyr Val Met Ala Ser Phe Tyr Lys Ala Glu
65                  70                  75                  80

Glu Leu Tyr
```

<210> SEQ ID NO 29
<211> LENGTH: 183
<212> TYPE: DNA
<213> ORGANISM: Homo sapiens
<220> FEATURE:
<221> NAME/KEY: misc_feature
<222> LOCATION: (183)..(183)
<223> OTHER INFORMATION: n is a, c, g, or t

<400> SEQUENCE: 29

```
agccatcttg tcaagtgtgc agagaaggag aaaactttct gtgtgaatgg aggcgagtgc    60
ttcatggtga aagacctttc aaatccctca agatacttgt gcaagtgccc aaatgagttt   120
actggtgatc gctgccaaaa ctacgtaatg ccagcttct acaaagcgga ggagctctac   180
can                                                                  183
```

<210> SEQ ID NO 30
<211> LENGTH: 61
<212> TYPE: PRT
<213> ORGANISM: Homo sapiens

<400> SEQUENCE: 30

```
Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30
```

```
Leu Cys Lys Cys Pro Asn Glu Phe Thr Gly Asp Arg Cys Gln Asn Tyr
         35                  40                  45

Val Met Ala Ser Phe Tyr Lys Ala Glu Glu Leu Tyr Gln
 50                  55                  60

<210> SEQ ID NO 31
<211> LENGTH: 50
<212> TYPE: PRT
<213> ORGANISM: Homo sapiens

<400> SEQUENCE: 31

Lys Cys Ala Glu Lys Glu Lys Thr Phe Cys Val Asn Gly Gly Glu Cys
  1               5                  10                  15

Phe Met Val Lys Asp Leu Ser Asn Pro Ser Arg Tyr Leu Cys Lys Cys
                 20                  25                  30

Pro Asn Glu Phe Thr Gly Asp Arg Cys Gln Asn Tyr Val Met Ala Ser
             35                  40                  45

Phe Tyr
     50

<210> SEQ ID NO 32
<211> LENGTH: 50
<212> TYPE: PRT
<213> ORGANISM: Homo sapiens

<400> SEQUENCE: 32

Lys Cys Ala Glu Lys Glu Lys Thr Phe Cys Val Asn Gly Gly Glu Cys
  1               5                  10                  15

Phe Met Val Lys Asp Leu Ser Asn Pro Ser Arg Tyr Leu Cys Lys Cys
                 20                  25                  30

Gln Pro Gly Phe Thr Gly Ala Arg Cys Thr Glu Asn Val Pro Met Lys
             35                  40                  45

Val Gln
     50

<210> SEQ ID NO 33
<211> LENGTH: 330
<212> TYPE: PRT
<213> ORGANISM: Homo sapiens

<400> SEQUENCE: 33

Met Arg Arg Asp Pro Ala Pro Gly Phe Ser Met Leu Leu Phe Gly Val
  1               5                  10                  15

Ser Leu Ala Cys Tyr Ser Pro Ser Leu Lys Ser Val Gln Asp Gln Ala
                 20                  25                  30

Tyr Lys Ala Pro Val Val Val Glu Gly Lys Val Gln Gly Leu Val Pro
             35                  40                  45

Ala Gly Gly Ser Ser Asn Ser Thr Arg Glu Pro Pro Ala Ser Gly
         50                  55                  60

Arg Val Ala Leu Val Lys Val Leu Asp Lys Trp Pro Leu Arg Ser Gly
 65                  70                  75                  80

Gly Leu Gln Arg Glu Gln Val Ile Ser Val Gly Ser Cys Val Pro Leu
                 85                  90                  95

Glu Arg Asn Gln Arg Tyr Ile Phe Phe Leu Glu Pro Thr Glu Gln Pro
                100                 105                 110

Leu Val Phe Lys Thr Ala Phe Ala Pro Leu Asp Thr Asn Gly Lys Asn
            115                 120                 125
```

```
Leu Lys Lys Glu Val Gly Lys Ile Leu Cys Thr Asp Cys Ala Thr Arg
    130                 135                 140

Pro Lys Leu Lys Lys Met Lys Ser Gln Thr Gly Gln Val Gly Glu Lys
145                 150                 155                 160

Gln Ser Leu Lys Cys Glu Ala Ala Gly Asn Pro Gln Pro Ser Tyr
                165                 170                 175

Arg Trp Phe Lys Asp Gly Lys Glu Leu Asn Arg Ser Arg Asp Ile Arg
            180                 185                 190

Ile Lys Tyr Gly Asn Gly Arg Lys Asn Ser Arg Leu Gln Phe Asn Lys
        195                 200                 205

Val Lys Val Glu Asp Ala Gly Glu Tyr Val Cys Glu Ala Glu Asn Ile
210                 215                 220

Leu Gly Lys Asp Thr Val Arg Gly Arg Leu Tyr Val Asn Ser Val Ser
225                 230                 235                 240

Thr Thr Leu Ser Ser Trp Ser Gly His Ala Arg Lys Cys Asn Glu Thr
                245                 250                 255

Ala Lys Ser Tyr Cys Val Asn Gly Val Cys Tyr Tyr Ile Glu Gly
            260                 265                 270

Ile Asn Gln Leu Ser Cys Lys Cys Pro Asn Gly Phe Phe Gly Gln Arg
        275                 280                 285

Cys Leu Glu Lys Leu Pro Leu Arg Leu Tyr Met Pro Asp Pro Lys Gln
290                 295                 300

Ser Val Leu Trp Asp Thr Pro Gly Thr Gly Val Ser Ser Ser Gln Trp
305                 310                 315                 320

Ser Thr Ser Pro Ser Thr Leu Asp Leu Asn
                325                 330

<210> SEQ ID NO 34
<211> LENGTH: 298
<212> TYPE: PRT
<213> ORGANISM: Homo sapiens

<400> SEQUENCE: 34

Met Arg Arg Asp Pro Ala Pro Gly Phe Ser Met Leu Leu Phe Gly Val
1               5                   10                  15

Ser Leu Ala Cys Tyr Ser Pro Ser Leu Lys Ser Val Gln Asp Gln Ala
                20                  25                  30

Tyr Lys Ala Pro Val Val Glu Gly Lys Val Gln Gly Leu Val Pro
            35                  40                  45

Ala Gly Gly Ser Ser Ser Asn Ser Thr Arg Glu Pro Pro Ala Ser Gly
    50                  55                  60

Arg Val Ala Leu Val Lys Val Leu Asp Lys Trp Pro Leu Arg Ser Gly
65                  70                  75                  80

Gly Leu Gln Arg Glu Gln Val Ile Ser Val Gly Ser Cys Val Pro Leu
                85                  90                  95

Glu Arg Asn Gln Arg Tyr Ile Phe Phe Leu Glu Pro Thr Glu Gln Pro
            100                 105                 110

Leu Val Phe Lys Thr Ala Phe Ala Pro Leu Asp Thr Asn Gly Lys Asn
        115                 120                 125

Leu Lys Lys Glu Val Gly Lys Ile Leu Cys Thr Asp Cys Ala Thr Arg
    130                 135                 140

Pro Lys Leu Lys Lys Met Lys Ser Gln Thr Gly Gln Val Gly Glu Lys
145                 150                 155                 160

Gln Ser Leu Lys Cys Glu Ala Ala Gly Asn Pro Gln Pro Ser Tyr
                165                 170                 175
```

Arg Trp Phe Lys Asp Gly Lys Glu Leu Asn Arg Ser Arg Asp Ile Arg
            180                 185                 190

Ile Lys Tyr Gly Asn Gly Arg Lys Asn Ser Arg Leu Gln Phe Asn Lys
        195                 200                 205

Val Lys Val Glu Asp Ala Gly Glu Tyr Val Cys Glu Ala Glu Asn Ile
    210                 215                 220

Leu Gly Lys Asp Thr Val Arg Gly Arg Leu Tyr Val Asn Ser Val Ser
225                 230                 235                 240

Thr Thr Leu Ser Ser Trp Ser Gly His Ala Arg Lys Cys Asn Glu Thr
                245                 250                 255

Ala Lys Ser Tyr Cys Val Asn Gly Gly Val Cys Tyr Tyr Ile Glu Gly
            260                 265                 270

Ile Asn Gln Leu Ser Cys Lys Cys Pro Val Gly Tyr Thr Gly Asp Arg
        275                 280                 285

Cys Gln Gln Phe Ala Met Val Asn Phe Ser
    290                 295

<210> SEQ ID NO 35
<211> LENGTH: 63
<212> TYPE: PRT
<213> ORGANISM: Homo sapiens

<400> SEQUENCE: 35

Thr Ser His Leu Val Lys Cys Ala Glu Lys Glu Lys Thr Phe Cys Val
1               5                   10                  15

Asn Gly Gly Glu Cys Phe Met Val Lys Asp Leu Ser Asn Pro Ser Arg
            20                  25                  30

Tyr Leu Cys Lys Cys Pro Asn Glu Phe Thr Gly Asp Arg Cys Gln Asn
        35                  40                  45

Tyr Val Met Ala Ser Phe Tyr Lys Ala Glu Glu Leu Tyr Gln Lys
    50                  55                  60

<210> SEQ ID NO 36
<211> LENGTH: 61
<212> TYPE: PRT
<213> ORGANISM: Homo sapiens

<400> SEQUENCE: 36

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser Phe Tyr Lys Ala Glu Glu Leu Tyr Gln
    50                  55                  60

<210> SEQ ID NO 37
<211> LENGTH: 60
<212> TYPE: PRT
<213> ORGANISM: Homo sapiens

<400> SEQUENCE: 37

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

```
Leu Cys Lys Cys Pro Asn Glu Phe Thr Gly Asp Arg Cys Gln Asn Tyr
         35                  40                  45

Val Met Ala Ser Phe Tyr Lys Ala Glu Glu Leu Tyr
         50                  55                  60

<210> SEQ ID NO 38
<211> LENGTH: 71
<212> TYPE: PRT
<213> ORGANISM: Homo sapiens

<400> SEQUENCE: 38

Thr Ser His Leu Val Lys Cys Ala Glu Lys Glu Lys Thr Phe Cys Val
1               5                   10                  15

Asn Gly Gly Glu Cys Phe Met Val Lys Asp Leu Ser Asn Pro Ser Arg
            20                  25                  30

Tyr Leu Cys Lys Cys Pro Asn Glu Phe Thr Gly Asp Arg Cys Gln Asn
        35                  40                  45

Tyr Val Met Ala Ser Phe Tyr Lys His Leu Gly Ile Glu Phe Met Glu
    50                  55                  60

Ala Glu Glu Leu Tyr Gln Lys
65                  70

<210> SEQ ID NO 39
<211> LENGTH: 50
<212> TYPE: PRT
<213> ORGANISM: Homo sapiens

<400> SEQUENCE: 39

Lys Cys Ala Glu Lys Glu Lys Thr Phe Cys Val Asn Gly Gly Glu Cys
1               5                   10                  15

Phe Met Val Lys Asp Leu Ser Asn Pro Ser Arg Tyr Leu Cys Lys Cys
            20                  25                  30

Pro Asn Glu Phe Thr Gly Asp Arg Cys Gln Asn Tyr Val Met Ala Ser
        35                  40                  45

Phe Tyr
    50

<210> SEQ ID NO 40
<211> LENGTH: 50
<212> TYPE: PRT
<213> ORGANISM: Homo sapiens

<400> SEQUENCE: 40

Lys Cys Ala Glu Lys Glu Lys Thr Phe Cys Val Asn Gly Gly Glu Cys
1               5                   10                  15

Phe Met Val Lys Asp Leu Ser Asn Pro Ser Arg Tyr Leu Cys Lys Cys
            20                  25                  30

Pro Asn Glu Phe Thr Gly Asp Arg Cys Gln Asn Tyr Val Met Ala Ser
        35                  40                  45

Phe Tyr
    50

<210> SEQ ID NO 41
<211> LENGTH: 69
<212> TYPE: PRT
<213> ORGANISM: Homo sapiens
```

```
<400> SEQUENCE: 41

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser Phe Tyr Lys His Leu Gly Ile Glu Phe Met Glu Lys
50                  55                  60

Ala Glu Glu Leu Tyr
65

<210> SEQ ID NO 42
<211> LENGTH: 50
<212> TYPE: PRT
<213> ORGANISM: Homo sapiens

<400> SEQUENCE: 42

Lys Cys Ala Glu Lys Glu Lys Thr Phe Cys Val Asn Gly Gly Glu Cys
1               5                   10                  15

Phe Met Val Lys Asp Leu Ser Asn Pro Ser Arg Tyr Leu Cys Lys Cys
            20                  25                  30

Pro Asn Glu Phe Thr Gly Asp Arg Cys Gln Asn Tyr Val Met Ala Ser
        35                  40                  45

Phe Tyr
    50

<210> SEQ ID NO 43
<211> LENGTH: 65
<212> TYPE: PRT
<213> ORGANISM: Homo sapiens

<400> SEQUENCE: 43

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Gln Pro Gly Phe Thr Gly Ala Arg Cys Thr Glu Asn
        35                  40                  45

Val Pro Met Lys Val Gln Asn Gln Glu Lys Ala Glu Glu Leu Tyr Gln
50                  55                  60

Lys
65

<210> SEQ ID NO 44
<211> LENGTH: 63
<212> TYPE: PRT
<213> ORGANISM: Homo sapiens

<400> SEQUENCE: 44

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Gln Pro Gly Phe Thr Gly Ala Arg Cys Thr Glu Asn
        35                  40                  45

Val Pro Met Lys Val Gln Thr Gln Glu Lys Ala Glu Glu Leu Tyr
50                  55                  60
```

```
<210> SEQ ID NO 45
<211> LENGTH: 50
<212> TYPE: PRT
<213> ORGANISM: Homo sapiens

<400> SEQUENCE: 45

Lys Cys Ala Glu Lys Glu Lys Thr Phe Cys Val Asn Gly Gly Glu Cys
1               5                   10                  15

Phe Met Val Lys Asp Leu Ser Asn Pro Ser Arg Tyr Leu Cys Lys Cys
            20                  25                  30

Gln Pro Gly Phe Thr Gly Ala Arg Cys Thr Glu Asn Val Pro Met Lys
        35                  40                  45

Val Gln
    50

<210> SEQ ID NO 46
<211> LENGTH: 50
<212> TYPE: PRT
<213> ORGANISM: Homo sapiens

<400> SEQUENCE: 46

Lys Cys Ala Glu Lys Glu Lys Thr Phe Cys Val Asn Gly Gly Glu Cys
1               5                   10                  15

Phe Met Val Lys Asp Leu Ser Asn Pro Ser Arg Tyr Leu Cys Lys Cys
            20                  25                  30

Gln Pro Gly Phe Thr Gly Ala Arg Cys Thr Glu Asn Val Pro Met Lys
        35                  40                  45

Val Gln
    50

<210> SEQ ID NO 47
<211> LENGTH: 83
<212> TYPE: PRT
<213> ORGANISM: Homo sapiens

<400> SEQUENCE: 47

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Gln Pro Gly Phe Thr Gly Ala Arg Cys Thr Glu Asn
        35                  40                  45

Val Pro Met Lys Val Gln Thr Gln Glu Lys Cys Pro Asn Glu Phe Thr
    50                  55                  60

Gly Asp Arg Cys Gln Asn Tyr Val Met Ala Ser Phe Tyr Lys Ala Glu
65                  70                  75                  80

Glu Leu Tyr

<210> SEQ ID NO 48
<211> LENGTH: 88
<212> TYPE: PRT
<213> ORGANISM: Homo sapiens

<400> SEQUENCE: 48

Ser His Leu Val Lys Cys Ala Glu Lys Glu Lys Thr Phe Cys Val Asn
1               5                   10                  15

Gly Gly Glu Cys Phe Met Val Glu Asp Leu Ser Asn Pro Ser Arg Tyr
            20                  25                  30
```

```
Leu Cys Lys Cys Gln Pro Gly Phe Thr Gly Ala Arg Cys Thr Glu Asn
         35                  40                  45

Val Pro Met Lys Val Gln Thr Gln Glu Lys Cys Pro Asn Glu Phe Thr
 50                  55                  60

Gly Asp Arg Cys Gln Asn Tyr Val Met Ala Ser Phe Tyr Ser Thr Ser
 65                  70                  75                  80

Thr Pro Phe Leu Ser Leu Pro Glu
                 85

<210> SEQ ID NO 49
<211> LENGTH: 31
<212> TYPE: PRT
<213> ORGANISM: Homo sapiens

<400> SEQUENCE: 49

Lys Cys Ala Glu Lys Glu Lys Thr Phe Cys Val Asn Gly Gly Glu Cys
 1               5                  10                  15

Phe Met Val Lys Asp Leu Ser Asn Pro Ser Arg Tyr Leu Cys Lys
                 20                  25                  30

<210> SEQ ID NO 50
<211> LENGTH: 61
<212> TYPE: PRT
<213> ORGANISM: Homo sapiens

<400> SEQUENCE: 50

Lys Cys Ala Glu Lys Glu Lys Thr Phe Cys Val Asn Gly Gly Glu Cys
 1               5                  10                  15

Phe Met Val Lys Asp Leu Ser Asn Pro Ser Arg Tyr Leu Cys Lys Cys
                 20                  25                  30

Pro Asn Glu Phe Thr Gly Asp Arg Cys Gln Asn Tyr Val Met Ala Ser
         35                  40                  45

Phe Tyr Ser Thr Ser Thr Pro Phe Leu Ser Leu Pro Glu
 50                  55                  60

<210> SEQ ID NO 51
<211> LENGTH: 61
<212> TYPE: PRT
<213> ORGANISM: Homo sapiens

<400> SEQUENCE: 51

Lys Cys Ala Glu Lys Glu Lys Thr Phe Cys Val Asn Gly Gly Glu Cys
 1               5                  10                  15

Phe Met Val Lys Asp Leu Ser Asn Pro Ser Arg Tyr Leu Cys Lys Cys
                 20                  25                  30

Pro Asn Glu Phe Thr Gly Asp Arg Cys Gln Asn Tyr Val Met Ala Ser
         35                  40                  45

Phe Tyr Ser Thr Ser Thr Pro Phe Leu Ser Leu Pro Glu
 50                  55                  60

<210> SEQ ID NO 52
<211> LENGTH: 65
<212> TYPE: PRT
<213> ORGANISM: Homo sapiens

<400> SEQUENCE: 52

Ser His Leu Val Lys Cys Ala Glu Lys Glu Lys Thr Phe Cys Val Asn
 1               5                  10                  15

Gly Gly Glu Cys Phe Met Val Lys Asp Leu Ser Asn Pro Ser Arg Tyr
                 20                  25                  30
```

```
Leu Cys Lys Cys Pro Asn Glu Phe Thr Gly Asp Arg Cys Gln Asn Tyr
        35                  40                  45

Val Met Ala Ser Phe Tyr Ser Thr Ser Thr Pro Phe Leu Ser Leu Pro
    50                  55                  60

Glu
65

<210> SEQ ID NO 53
<211> LENGTH: 53
<212> TYPE: PRT
<213> ORGANISM: Homo sapiens

<400> SEQUENCE: 53

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
                20                  25                  30

Cys Val Val Gly Tyr Ile Gly Glu Arg Cys Gln Tyr Arg Asp Leu Lys
            35                  40                  45

Trp Trp Glu Leu Arg
    50
```